US007435718B2

(12) United States Patent
Tudan et al.

(10) Patent No.: US 7,435,718 B2
(45) Date of Patent: Oct. 14, 2008

(54) CXCR4 ANTAGONIST TREATMENT OF HEMATOPOIETIC CELLS

(75) Inventors: Christopher R. Tudan, Vancouver (CA); Ahmed Merzouk, Richmond (CA); Lakhdar Arab, Vancouver (CA); Geeta Saxena, Vancouver (CA); Connie J. Eaves, Vancouver (CA); Johanne Cashman, Vancouver (CA); Ian Clark-Lewis, deceased, late of Vancouver (CA); by Mary A. Richter, legal representative, Vancouver (CA); by Michael Clark-Lewis, legal representative, Northbridge (AU); Hassan Salari, Delta (CA)

(73) Assignees: Chemokine Therapeutics Corp. (CA); The University of British Columbia (CA)

( * ) Notice: Subject to any disclaimer, the term of this patent is extended or adjusted under 35 U.S.C. 154(b) by 335 days.

(21) Appl. No.: 10/945,674

(22) Filed: Sep. 20, 2004

(65) Prior Publication Data

US 2006/0014682 A1 Jan. 19, 2006

Related U.S. Application Data

(63) Continuation of application No. 09/852,424, filed on May 9, 2001, now abandoned.

(60) Provisional application No. 60/205,467, filed on May 19, 2000.

(30) Foreign Application Priority Data

May 9, 2000 (CA) .................................... 2305787

(51) Int. Cl.

| | |
|---|---|
| ***A61K 38/16*** | (2006.01) |
| *A61K 38/10* | (2006.01) |
| *A61K 38/07* | (2006.01) |
| *C07K 2/00* | (2006.01) |
| *C07K 14/00* | (2006.01) |
| *C07K 7/08* | (2006.01) |
| *C07K 5/10* | (2006.01) |

(52) U.S. Cl. ............................... 514/12; 514/2; 514/13; 514/14; 514/18; 530/300; 530/324; 530/326; 530/327; 530/330

(58) Field of Classification Search ....................... None
See application file for complete search history.

(56) References Cited

U.S. PATENT DOCUMENTS

| | | | | |
|---|---|---|---|---|
| 2,530,369 | A | 11/1950 | Simons | |
| 2,760,992 | A | 8/1956 | Schoeffel et al. | |
| 4,554,101 | A | 11/1985 | Hopp | |
| 4,868,116 | A | 9/1989 | Morgan et al. | |
| 4,980,286 | A | 12/1990 | Morgan et al. | |
| 5,082,670 | A | 1/1992 | Gage et al. | |
| 5,166,320 | A | 11/1992 | Wu et al. | |
| 5,350,836 | A | 9/1994 | Kopchick et al. | |
| 5,399,346 | A | 3/1995 | Anderson et al. | |
| 5,401,651 | A | 3/1995 | Walz | |
| 5,563,048 | A | 10/1996 | Honjo et al. | |
| 5,756,084 | A | 5/1998 | Honjo et al. | |
| 5,807,744 | A | 9/1998 | Berneman et al. | |
| 5,856,301 | A | 1/1999 | Craig et al. | |
| 5,871,723 | A | 2/1999 | Strieter et al. | |
| 5,919,776 | A | 7/1999 | Hagmann et al. | |
| 5,962,462 | A | 10/1999 | Mills et al. | |
| 5,990,163 | A | 11/1999 | Evans et al. | |
| 6,013,644 | A | 1/2000 | Mills et al. | |
| 6,022,848 | A | 2/2000 | Kozlov et al. | |
| 6,046,185 | A | 4/2000 | Burgoyne et al. | |
| 6,124,319 | A | 9/2000 | MacCoss et al. | |
| 6,132,987 | A | 10/2000 | Charo et al. | |
| 6,133,319 | A | 10/2000 | Widdowson | |
| 6,136,827 | A | 10/2000 | Caldwell et al. | |
| 6,140,349 | A | 10/2000 | Caldwell et al. | |
| 6,166,037 | A | 12/2000 | Budhu et al. | |
| 6,204,294 | B1 | 3/2001 | Bryan et al. | |
| 6,356,887 | B1 | 3/2002 | Berenson et al. | |
| 6,515,001 | B2 | 2/2003 | Saxena et al. | |
| 6,613,742 | B1 * | 9/2003 | Huang et al. | 514/12 |
| 6,693,134 | B2 | 2/2004 | Saxena et al. | |
| 6,875,738 | B1 | 4/2005 | Clarke Lewis et al. | |
| 6,946,445 | B1 | 9/2005 | Clarke Lewis et al. | |
| 2002/0156034 | A1 | 10/2002 | Tudan et al. | |
| 2002/0165123 | A1 | 11/2002 | Tudan et al. | |
| 2003/0004136 | A1 | 1/2003 | Saxena et al. | |

(Continued)

FOREIGN PATENT DOCUMENTS

WO WO 89/02468 3/1989

(Continued)

OTHER PUBLICATIONS

J. Rudinger. In: Peptide Hormones, JA Parsons, Ed. (1976) 1-7.*

(Continued)

*Primary Examiner*—Andrew D Kosar
(74) *Attorney, Agent, or Firm*—TIPS Group; Brian S. Boyer

(57) ABSTRACT

In accordance with various aspects of the invention, CXCR4 antagonists may be used to treat hematopoietic cells, such as progenitor or stem cells, to promote the rate of cellular multiplication, self-renewal, proliferation or expansion. CXCR4 antagonists may be used therapeutically to stimulate hematopoietic stem/progenitor cell multiplication/self-renewal.

14 Claims, 3 Drawing Sheets

U.S. PATENT DOCUMENTS

| | | | |
|---|---|---|---|
| 2003/0045550 | A1 | 3/2003 | Saxena et al. |
| 2003/0092674 | A1 | 5/2003 | Saxena et al. |
| 2003/0125380 | A1 | 7/2003 | Saxena et al. |
| 2003/0148940 | A1 | 8/2003 | Tudan et al. |
| 2002/0202963 | | 10/2003 | Crystal et al. |
| 2005/0059584 | A1 | 3/2005 | Merzouk et al. |
| 2005/0164935 | A1 | 7/2005 | Clarke Lewis et al. |
| 2005/0265969 | A1 | 12/2005 | Clarke Lewis et al. |
| 2006/0014682 | A1 | 1/2006 | Clarke Lewis et al. |

FOREIGN PATENT DOCUMENTS

| | | |
|---|---|---|
| WO | WO 89/05345 | 6/1989 |
| WO | WO 89/07136 | 8/1989 |
| WO | WO 90/06757 | 6/1990 |
| WO | WO 91/04274 | 4/1991 |
| WO | WO 92/07573 | 5/1992 |
| WO | WO 93/10234 | 5/1993 |
| WO | WO 93/13206 | 7/1993 |
| WO | WO 95/05452 | 2/1995 |
| WO | WO 95/09236 | 4/1995 |
| WO | WO 96/40772 | 12/1996 |
| WO | WO 97/28257 | 8/1997 |
| WO | WO 97/28258 | 8/1997 |
| WO | WO 98/04684 | 2/1998 |
| WO | WO 98/04698 | 2/1998 |
| WO | WO 98/09642 | 3/1998 |
| WO | WO 98/51705 | 11/1998 |
| WO | WO 99/47158 | 9/1999 |
| WO | WO 00/09152 | 2/2000 |
| WO | WO 00/66112 | 9/2000 |
| WO | WO 01/76615 | 10/2001 |
| WO | WO 01/85196 | 11/2001 |
| WO | WO 2004/024088 A2 | 3/2004 |

OTHER PUBLICATIONS

S. Nema et al. PDA J. Pharm. Sci. Tech. (1997) 51, pp. 166-171.*
U.S. Appl. No. 10/932,208, filed Aug. 31, 2004, Merzouk et al.
U.S. Appl. No. 10/243,795, filed Sep. 13, 2002, Merzouk et al.
Acsadi, G., et al., *Nature* 352:815-818, (1991).
Aiuti, A., et al., *J. Exp. Med.* 185(1):111-120, (1997).
Aiuti, A., et al., *Eur. J. Immunol.* 29:1823-1831, (1999).
Alkhatib, G. et al., *Science* 272:1955-1958, (1996).
Allen, M. et al., *J. Biomolecular Screening* 5(2):63-69, (2000).
Alleva, D., et al., *J. Immunol.* 161(12):6878-6884, (1998).
Anderlini, P., et al., *Blood* 90(3), 903-908, (1997).
Anderson, W., et al., *Science* 288:627-629, (2000).
Arenzana-Selsdedos, F., et al., *Nature* 383:400, (1996).
Armentano, D., et al., *Proc. Nat'l. Acad. Sci.* 87:6141-6145, (1990).
Ausubel, et al., *Current Protocols in Mol. Biol. Supp.* 36:9.10.1-9.14.6, (1995).
Avenarius, H., et al., *Inter. J. Hematology* 58:189-196, (1993).
Baggiolini, M., *Nature* 392:565-568, (1998).
Baird, A., et al., *Current Opinion in Immunology* 11:157-166, (1999).
Balasa, B., et al., *J. Exp. Med.* 186:385-391, (1997).
Baldari, et al., *The EMBO J.* 6(1):229-234, (1987).
Barbier, J., et al., *J. Med. Chem.* 40(9):1373-1380, (1997).
Barbier, J., et al., *Biochemistry* 39(47):14522-14530, (2000).
Banerji, et al., *Cell* 33:729-740, (1983).
Barnes, D., et al., *J. Clin. Invest.* 101(12):2910-2919, (1998).
Belperio, et al., *J. Leukoc. Biol.* 68:1-8, (2000).
Benoist, et al., *Nature* 290:304-310, (1981).
Berkner, K., *Biotechinques* 6(7):616-628, (1988).
van Beuschem, V., et al., *Proc. Nat'l. Acad. Sci* 89:7640-7644, (1992).
Blease, K., et al., *J. Immunol.* 165:1564-1572, (2000).
Bleul, C., et al., *J. Exp. Med.* 184:1101-1109, (1996).
Bleul, C., et al., *Nature* 382:829-832, (1996).
Bollon, et al., *J. of Clinical Hemotology and Oncology* 10:39-48, (1980).
Bork, et al., *Trends in Genetics* 12(10):425-427, (1996).
Bork, A., *Genome Res.* 10:398-400, (2000).
Botstein, et al., "Making Mutations in Vitro and Putting them Back Into Yeast", Dept of Biol. Massachussetts Institute of Technology, 265-274, (1982).
Brandt, J., et al., *J. Clin Invest.* 86:932-941, (1990).
Brandt, J., et al., *Blood* 79(3):634-641, (1992).
Brandt, J., et al., *J. Clin. Invest.* 82:1017-1027, (1998).
Brenner, S.E., *Trends in Genetics* 15(4):132-133, (1999).
Broach, J.R., *The Molecular Biology of the Yeast Saccharomyces*, 445-470, (1981).
Broach, J.R., *Cell* 28:203-204, (1982).
Buckley, C., et al., *J. Immunol.* 165:3423-3429, (2000).
Burt, R., *Stem Cells* 17(6):366-372, (1999).
Buser, et al., *Methods in Molecular Biology* 138:143-148, (2000).
Calame, et al., *Advances in Immunology* 43:236-275, (1988).
Campbell, J., et al., *Science* 279:381-383, (1998).
Camper, et al., *Genes & Development 3*, 537-546, (1989).
Carr, M., et al., *Proc. Nat'l. Acad. Sci.* 91:3652-3656, (1994).
Cashman, J., et al., *Blood* 94(11):3722-3729, (1999).
Cavazzano-Calvo, M., et al., *Science* 288:669-672, (2000).
Cenatiempo, Y., *Biochimie* 68:505-515, (1986).
Charo, I., et al., *Proc. Natl. Acad. Sci.* 91:2752-2756, (1994).
Choe, H., et al., *Cell* 85:1135-1148, (1996).
Chowdury, J., et al., *Science* 254:1802-1805, (1991).
Clapp, W., et al., *Blood* 78(4):1132-1139, (1991).
Clark-Lewis, I., et al., *J. Biol. Chem.* 269(23):16075-16081, (1994).
Cocchi, F., et al., *Science* 270:1811-1815, (1995).
Colosimo, et al., *BioTechniques* 29:314-331, (2000).
Combadiere, C., et al., *J. Biol. Chem.* 270:16491-16494, (1995).
Conti, J., et al., *Cancer* 70(11):2699-2702, (1992).
Cristiano, R., et al., *Proc. Nat'l. Acad. Sci.* 90:2122-2126, (1993).
Crump, M., et al., *EMBO Journal* 16(23):6996-7007, (1997).
Curiel, D., et al., *Proc. Nat'l. Acad. Sci.* 88:8850-8854, (1991).
Cushing, S., et al., *Proc. Nat'l. Acad. Sci.* 87:5134-5138, (1990).
Cwirla, S., et al., *Science* 276:1696-1699, (1997).
Dai, Y., et al., *Proc. Nat'l. Acad. Sci.* 89:10892-10895, (1992).
Danos, O., et al., *Proc, Nat'l. Acad. Sci.* 85:6460-6464, (1988).
Daugherty, et al., *Chemokine Protocols* 138:129-148, (2000).
Daugherty, et al., *Methods in Molecular Biology* 138:129-134, (2000).
Demirer, T., et al., *Stem Cells* 14:106-116, (1996).
DeNardo, et al., *Cancer* 94:1275-1286, (2002).
Deng, H., et al., *Nature* 381:661-666, (1996).
Dhib-Jalbut, S., et al., *Journal of Interferon and Cytokine Research* 16:195-200, (1996).
Di Salvo, J., et al., *Eur. J. Pharm.* 409:143-154, (2000).
Doerks, et al., *Trends in Genetics* 14(6):248-250, (1998).
Doranz, B., et al., *Cell* 85:1149-1158, (1996).
Dragic, T., et al., *Nature* 381:667-673, (1996).
Dufour, J.H., et al., *The Journal of Immunology* 167(7077-7083):3195-3204, (2001).
Dunican, A., et al., *Shock* 13(3):244-250, (2000).
Durig, J., et al., *Leukemia* 14:1652-1660, (2000).
Eck et al., Goodman & Gilman's The Phrmacological Basis of Therapeutics, 9th Edition, Chapter 5, McGraw-Hill, NY (1996).
Edlund, et al., *Science* 230:912-916, (1985).
Eglitis, M., et al., *Science* 320:1395-1398, (1985).
Elisseeva, E., et al., *J. Biol. Chem.* 275(35):26799-26805, (2000).
Elseviers, M. et al., *Biochem. And Biophys. Research Comm.* 154(2)515-521, (1998).
Emanueli et al., *Br. J. Pharmacol.*, 133(7):951-958 (2001).
Gottesman, S., *Methods in Enzymology*, 185:119-129, (1990).
Federsppiel, B., et al., *Genomics* 16:707-712, (1993).
Feng, Y., et al., *Science* 272:872-877, (1996).
Ferry, N. et al., *Proc. Nat'l. Acad. Sci.*, 88:8377-8381, (1991).
Fletcher, F., et al., *Blood* 76(6):1098-1103, (1990).
Flotte, T., et al., *Am. J. Respir. Cell Mol. Biol.* 7:349-356, (1992).
Flotte, T., et al., *J. Biol. Chem.* 268(5):3781-3790, (1993).
Francis, et al., *International Journal of Hematology* 68:1-18, (1998).
Furuichi, K., et al., *Am. J. Nephrol.* 20:291-299, (2000).
Gazitt, *J. Hematother. Stem Cell. Res.* 10:229-236, (2001).
Gimbrone, M., et al., *Science* 246:1601-1603, (1989).
Girait, S., et al., *Blood* 89(12):4531-4536, (1997).
Glick, et al., *J. of Industrial Microbiology* 1:277-282, (1987).

Glimm, et al., *Blood* 99(9):3454-3457, (2002).
Gold, et al., *Ann Rev. Microbiol.* 35:365-403, (1981).
Gong, J. et al., *J. Biol. Chem.* 271(18):10521-10527, (1996).
Gonzalo et al., *J. Immunology*, 165(1):499-508 (2000).
Gottesman, S., *Ann. Rev. Genet.* 18:415-441, (1984).
Gupta, S. et al., *J. Biol. Chem.* 273(7):4232-4287, (1998).
Haas, R. et al., *Bone Marrow Transplantation*, 9:459-465, (1992).
Hamada, T., et al., *J. Exp. Med.* 188(3):539-548, (1998).
Hamer, et al., *J. of Molecular and Applied Genetics* 1:273-288, (1982).
Hartung, H. et al., *Ann. Neurol.* S57:S57-S63, (1990).
Hattori, et al., *Blood* 97:3354-3359, (2001).
Hébert, et al., *The J. of Biological Chemistry* 266(28):18989-18994, (1991).
Hermonat, P. et al., *Proc. Nat'l. Acad. Sci.* 81:6466-6470, (1984).
Herz, J., et al., *Proc. Nat'l. Acad. Sci.* 90:2812-2816, (1993).
Heissig et al., *Blood*, 94(1o Suppl):p. 100A (1999).
Heveker, N., et al., *Current Biology*, 8:369-376, (1998).
Ho, A., et al., *Leukemia*, 7(11):1738-1746, (1993).
Hodohara, K., et al., *Blood* 95(3):769-775, (2000).
Holmes, W., et al., *Science* 253(50):1278-1280, (1991).
Hooper, D., et al., *Proc. Nat'l. Acad. Sci.* 95:675-680, (1998).
Horuk, R., et al., *J. Biol. Chem.* 276(6):4199-4204, (2001).
Huang, S., et al., *Nature* 360:745-749, (1992).
Huber, A., et al., *Science* 254:99-102, (1991).
Huber, B., et al., *Proc. Nat'l. Acad Sci.* 88:8039-8043, (1991).
Hunter et al., *Blood*, 86(12):4400-4408 (1995).
Hwu, P., et al., *J. Immunol.* 150:4104-4115, (1993).
IFNB Multiple Sclerosis Study Group, *Neurology* 43:655-661, (1993).
Ikebe et al., *J. Biol. Chem.*, 273(8):17702-17707 (1998).
Ikebuchi, K., et al., *Nat. Acad. Sci.* 85(10):3445-3449, (2001).
Imai, T., et al., *J. Biol. Chem.* 272(23):15036-15042, (1997).
Imai, T., et al., *J. Biol. Chem.* 273(3):1765-1768, (1998).
John Jr., et al., *Reviews of Infectious Diseases* 8(5):693-704 (1986).
Johnston, et al., *Proc. Natl. Acad. Sci. USA* 79:6971-6975, (1982).
Jones, S., et al., *J. Biol. Chem.* 272(26):16166-16169, (1997).
Kaltsas, et al., *Ann. Oncol.* 12(Supp. 2)S47-50, (2001).
Kates, S., et al., *Analytical Biochemistry*, 212:303-310, (1993).
Kaufman, et al., *The EMBO J.* 6(1):187-193, (1987).
Kawachi, Y., et. al., *Brit. J. Hematology*, 94:413-416, (1996).
Kay, M., et al., *Human Gene Therapy* 3:647-647, (1992).
Kessel, et al., *Science* 249:374-379, (1990).
Kessinger, et al., *Bone Marrow Transplantation* 4:643-646, (1989).
Kieseier, et al., *Brain* 125:823-824, (2002).
Kim, C., et al., *J. Leukocyte Biology* 65:6-15, (1999).
Kitaura, M. et al., *J. Biol. Chem.* 271(13)7725-7730, (1996).
Koch, et al., *Science* 258:1798-1801, (1992).
Kowalska, M., et al., *Blood* 96(1):50-57, (2000).
Kramer, W., et al., *J. Biol. Chem.* 267(26)18598-18604, (1992).
Kume, A., et al., *Int. J. Hematology* 69:227-233, (1999).
Kurjan, J., et al., *Cell* 30:933-943, (1982).
Kuroiwa, M., et al., *Int. J. Hematology* 63:311-316, (1996).
Lane, et al., *Blood* 96:4152-4159, (2000).
Lasky, L., et al., *Transfusion* 21(3):247-260, (1981).
Lataillade, J., et al., *Blood* 95(3):756-768, (2000).
Law, P., *Exp. Hematol.* 11(5):351-357 , (1983).
Le Chevalier, T., *Eur. J. Cancer* 30A(3):410-412, (1994).
Leary, A., et al., *Blood* 71(6):1759-1763, (1988).
Lejeune, et al., *Cancer Immunol. Immunother.* 38:167-170, (1994).
Lemarchand, P., et al., *Nat. Acad. Sci.* 89(4):6482-6486, (1992).
Li, et al., *J. Biol. Chem.* 273(26):16442-16445, (1998).
Lin, T., et al., *J. Immunol.* 165:211-220, (2000).
Loetscher, M., et al., *J. Biol. Chem.* 269(1):232-237, (1994).
Loetscher, P. et al., *FASEB J.* 8:1055-1060, (1994).
Loetscher, P., et al., *J. Biol. Chem.* 273(35):22279-22283, (1998).
Lohrmann, H., et al., *B. J. Haematol.* 40:369-381, (1978).
Lombart, H., et al., *J. Org. Chem.* 59:6147-6149, (1994).
Luckow, et al., *Virology* 170:31-39, (1989).
Lukacs, N., et al., *J. Immunol.* 158:4398-4404, (1997).
Luo, J., et al., *Biochemical and Biophysical Research Communications* 264:42-47, (1999).
Mach, et al., *Curr. Opin. Immunol.* 12:571-575, (2000).
Maniatis, *Cell Biology* 3:564-608, (1980).
Marshall et al., *Science*, 269(5227):1050, 1052-1055, (1995).
Marshall, G. et al., *Tetrahedron* 49(17):3547-3558, (1993).
McKnight, S.L., *Cell* 31:355-365, (1982).
McLaughlin, S., et al., *J. Virology* 62(6):1963-1973, (1988).
Miller, et al., "An Insect Baculovirus Host-Vector System for High-Level Expression of Foreign Genes," 277-297, (1986).
Miller, et al., *J. Immunol.* 143(9):2907-2916, (1989).
Miller, D., *Blood* 76(2):271-278, (1990).
*Molecular Cloning A Laboratory Manual*, Third Ed., vol. 1, (2001).
Moss, T., et al., *Blood* 76(9):1879-1883, (1990).
Moss, J., *American Chem. Soc.* 18:423-448, (1995).
Murphy, P., et al., *Science* 258:1280-1283, (1991).
Muzyczka, N., *Current Topics in Microbiol. And Immunol.* 158:98-129, (1992).
Myers, S., et al., *J. Biol. Chem.* 270(11):5786-5792, (1995).
Nagai, U., et al., *Tetrahedron* 49(17):3577-3592, (1993).
Nagasawa, T., et al., *Proc. Nat'l. Acad Sci.* 91:2305-2309, (1994).
Nagasawa, T., et al., *Proc. Nat'l. Acad. Sci.* 93:14726-14729, (1996).
Nagasawa, T., et al., *Nature* 382:635-638, (1996).
Nagasawa, *Int. J. Hematol.* 72:408-411, (2000).
Nanki et al., *J. Immunology*, 165(11):6590-6598 (2000).
Neote, K., et al., *Cell* 72:415-425, (1993).
Nett et al., *Eur. J. Biochem.*, 267(18):5777-5782 (2000).
Ng, H., et al., *J. Med. Chem.* 42:4680-4694, (1999).
Ngo, et al., *The Protein Folding Problem and Tertiary Structure Prediction*, 492-495, (1994).
Nomura, et al., *Int. J. Cancer* 91:597-606, (2001).
Oberlin, E., et al., *Nature*, 382:833-835, (1996).
Orkin et al., Report and Recommendations of the Panel to assess the NIH Investment in Research on Gene Therapy, available through NIH or at http://www.nih.gov/news/panelrep (1995).
Peled, A., et al., *Science* 283:845-848, (1999).
Pettengell, R., et al., *Blood* 82(7):2239-2248, (1993).
Perez, et al., *Exp. Hematol.* 32:300-307, (2004).
Pinkert, et al., *Genes & Development* 1:268-276, (1987).
Ponath, et al., *Methods in Molecular Biology* 138:113-120, (2000).
Quantin, B., et al., *Proc. Nat'l. Acad. Sci.* 89:2581-2584, (1992).
Queen, et al., *Cell* 33:741-748, (1983).
Richman, C., et al., *Blood* 47(6):1031-1039, (1976).
Richmond, A., et al., *J. Cell Phys.* 129:375-384, (1986).
Ripka, W., et al., *Tetrahedron*, 49(17):3593-3608, (1993).
Rissanen et al., Gene Therapy for Therapeutic Angiogenesis in Critically Ischaemic Lower Limb-on the way to the clinic, *Eur. J. Clin Invest.*, 31(8):651-666 (2001).
Robinson et al., *Proc. Nat'l. Acad. Sci.*, 95(11):5929-5934 (1998).
Rosenfeld, M., et al., *Science* 252:431-434, (1991).
Rosenfeld, M., et al., *Cell* 68:143-155, (1992).
Ross, Gene Therapy in the United States: A Five-Year Status Report, *Hum. Gene Ther.*, 7(14):1781-1790 (1996).
Rubanyi, The Future of Human Gene Therapy, *Mol. Aspects Med.*, 22(3):113-142 (2001).
Rubin, G.M., *Science* 240:1453-1459, (1988).
Rudick, R., et al., *Neurology* 50(5):1294-1300, (1998).
Sabers, A., et al., *Acta. Neurol. Scand.* 92:19-27, (1995).
Sambrook, J., et al., *Cold Spring Harbor Laboratory Press*, (1989).
Samulski, R., et al., *J. Virology* 63(9):3822-3828, (1989).
Seed, B., *Nature* 329(29):840-842, (1987).
Schiffer, C., et al., *Ann. N.Y. Acad. Sci.* 161-169, (1983).
Schulz, L., et al., *Gene* 54:113-123, (1987).
Schwaab et al., Gene Therapy of Hemophilia, *Semin Thromb. Hemostat.*,27(4):417-424 (2001).
Schwarting, A., et al., *J. Immunol.* 161:494-503, (1998).
Schwarz, et al., *Nat. Rev. Drug Discov.* 1:347-358, (2002).
Shimoda, K., et al., *J. Clin. Invest.* 91(4):1310-1313, (1993).
Shirozu, M., et al., *Genomics* 28:495-500, (1995).
Siena, S., et al., *Blood* 74(6):1905-1914, (1989).
Silver, et al., *Proc. Natl. Acad. Sci. USA* 81:5951-5955, (1984).
Skolnick, et al., *Trends in Biotech* 18(1):34-39, (2000).
Smith, et al., *Molecular and Cellular Biology* 3(12):2156-2165, (1983).
Smith, et al., *Gene* 67:31-40, (1988).
Smith, et al., *Nature Biotech* 15:1222-1223, (1997).

Stiff, P., et al., *Transfusion* 23:500-503, (1983).
Strieter, M., et al., *Science* 253:1467-1469, (1989).
Strieter, R., et al., *J. Biol. Chem.* 264(18):10621-10626, (1989).
Tashiro, K., et al., *Science* 261:600-603, (1993).
Thelen, M., et al., *FASEB J.* 2:2702-2706, (1988).
To, L., et al., *Bone Marrow Transplantation* 9:277-284, (1992).
Tokuda, A., et al., *J. Immunol.* 164:2745-2751, (2000).
Tratschin, J., et al., *J. Virology* 51(3):611-619, (1984).
Tratschin, J., et al., *Mol. Cell Biol.* 4(10):2072-2081, (1984).
Tratschin, J., et al., *Mol. Cell Biol.* 5(11):3251-3260, (1985).
von Tscharner, V., et al., *Nature* 324:369-372, (1986).
Tsuji, T., et al., *Proc. Nat'l. Acad. Sci.* 87:8835-8839, (1990).
Tudan, et al., *J. Med. Chem* 45(10):2024-2031, (2002).
Unemori, E., et al., *J. Biol. Chem.* 268(2):1338-1342, (1992).
Van Leeuwen et al., *EMBO J.*, 15;16(8):2043-2053 (1997).
Verfaillie, C., et al., *J. Exp. Med.* 172:509-520, (1990).
Wada, et al., *Nucleic Acids Research* 20:2111-2118, (1992).
Wang, J., et al., *Blood* 92(3):756-764, (1998).
Wang, W., et al., *The Journal of Biological Chemistry* 275(29):23313-22323, (2000).
Warringa, R., et al., *Blood* 77(12):2694-2700, (1991).
Weber, F., et al., *Annals Neur.* 44(1):27-34, (1998).
Wells, J.A., *Biochemistry* 29(37):8509-8517, (1990).
Wess, G., et al., *Tetrahedron Letters*, 33(2):195-198, (1992).
Wess, G., et al., *Tetrahedron Letters*, 34(5):817-818, (1993).
Wilson, J., et al., Proc. Natl'l. Acad. Sci. 85:3014-3018, (1988).
Wilson, J., et al., *J. Biol. Chem.* 267(2):963-967, (1992).
Winoto, et al., *The EMBO J.* 8(3):729-733, (1989).
Wolfe, J., et al., *Science* 247:1465-1468, (1990).
Wondisford, F., et al., *Molecular Endocrinology* 2(1):32-39, (1988).
Wu, G., et al., *J. Biol. Chem.* 263(29):14621-14624, (1988).
Ying, S., et al., *J. Immunol.* 163:6321-6329, (1999).
Yla-Herttuala, S., et al., *Proc. Nat'l. Acad Sci.* 88:5252-5256, (1991).
Yu, C., et al., *Immunology* 95:480-487, (1998).
Zhong, et al., *Exp. Hematol* 32:470-475, (2004).
Zhou, N., et al., *Biochemistry 2000* 39:3782-3787, (2000).
Zhu, Y., et al., *SIGMOD Conference* 431-442, (2004).
Zsebo, K., et al., *Cell* 63:195-201, (1990).

* cited by examiner

CXCR4 ANTAGONIST TREATMENT OF HEMATOPOIETIC CELLS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

In one aspect, the invention relates to therapeutic uses of chemokine receptor antagonists, including peptide antagonists of CXC chemokine receptor 4 (CXCR4) for use in the treatment of hematopoietic cells in vitro and in vivo. In another aspect, the invention relates to novel CXCR4 antagonists which may be used in the treatment of hematopoietic cells.

BACKGROUND OF THE INVENTION

Cytokines are soluble proteins secreted by a variety of cells including monocytes or lymphocytes that regulate immune responses. Chemokines are a superfamily of chemoattractant proteins. Chemokines regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines. Two minor subgroups contain only one of the two cysteines (C) or have three amino acids between the cysteines ($CX_3C$). In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem, 269, 232-237), HUMSTR (Federsppiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877). CXCR4 is widely expressed on cells of hemopoietic origin, and is a major co-receptor with $CD^4$ for human immunodeficiency virus 1 (HIV-1) Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877).

Chemokines are thought to mediate their effect by binding to seven transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF-1) is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1α (SDF-1α) and stromal cell derived factor-1β (SDF-1β) are closely related (together referred to herein as SDF-1). The native amino acid sequences of SDF-1α and SDF-1β are known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 Kb. SDF-1 was initially characterized as a pre-B cell-stimulating factor and as a highly efficient chemotactic factor for T cells and monocytes (Bieul et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with parinatal lethality, including abnormalities in cardiac development, B-cell lymphopoiesis, and bone marrow myelopoiesis (Nagasawa et al. (1996) Nature 382:635-637).

SDF-1 is functionally distinct from other chemokines in that it is reported to have a fundamental role in the trafficking, export and homing of bone marrow progenitor cells (Aiuti, A., Webb, I. J., Bleul, C., Springer, T:, and Guierrez-Ramos, J. C., (1996) J. Exp. Med. 185, 111-120 and Nagasawa, T., Hirota, S., Tachibana, K., Takakura N., Nishikawa, S.-I., Kitamura, Y., Yoshida, N., Kikutani, H., and Kishimoto, T., (1996) Nature 382, 635-638). SDF-1 is also structurally distinct in that it has only about 22% amino acid sequence identity with other CXC chemokines (Bleul, C. C., Fuhlbrigge, R. C., Casasnovas, J. M., Aiuti, A., and Springer, T. A., (1996) J. Exp. Med. 184, 1101-1109). SDF-1 appears to be produced constitutively by several cell types, and particularly high levels are found in bone-marrow stromal cells (Shirozu, M., Nakano, T., Inazawa, J., Tashiro, K., Tada, H. Shinohara, T., and Honjo, T., (1995) Genomics, 28, 495-500 and Bleul, C. C., Fuhlbrigge, R. C., Casasnovas, J. M., Aiuti, A., and Springer, T. A., (1996) J. Exp. Med. 184, 1101-1109). A basic physiological role for SDF-1 is implied by the high level of conservation of the SDF-1 sequence between species. In vitro, SDF-1 stimulates chemotaxis of a wide range of cells including monocytes and bone marrow derived progenitor cells (Aiuti, A., Webb, U., Bleul, C., Springer, T., and Guierrez-Ramos, J. C., (1996) J. Exp. Med. 185, 111-120 and Bleul, C. C., Fuhlbrigge, R. C., Casasnovas, J. M., Aiuti, A., and Springer, T. A., (1996) J. Exp. Med. 184, 1101-1109). SDF-1 also stimulates a high percentage of resting and activated T-lymphocytes (Bleul, C. C., Fuhlbrigge, R. C., Casasnovas, J. M., Aiuti, A., and Springer, T. A., (1996) J. Exp. Med. 184, 1101-1109 and Campbell, J. J., Hendrick, J., Zlotnik, A., Siani, M. A., Thompson, D. A., and Butcher, E. C., (1998) Science, 279 381-383).

Native SDF-1 has been demonstrated to induce the maturation and activation of platelets (Hamada T. et al., J. Exp. Med. 188, 638-548 (1998); Hodohara K. et al., Blood 95, 769-775 (2000); Kowalska M. A. et al., Blood 96, 50-57 (2000)), and CXCR4 is expressed on the megakaryocytic lineage cells (CFUOMeg) (Wang J-F. et al., Blood 92, 756-764 (1998)).

A variety of diseases require treatment with agents that are preferentially cytotoxic to dividing cells. Cancer cells, for example, may be targeted with cytotoxic doses of radiation or chemotherapeutic agents. A significant side-effect of this approach to cancer therapy is the pathological impact of such treatments on rapidly dividing normal cells. These normal cells may for example include hair follicles, mucosal cells and the hematopoietic cells, such as primitive bone marrow progenitor cells and stem cells. The indiscriminate destruction of hematopoietic stem, progenitor or precursor cells can lead to a reduction in normal mature blood cell counts, such as leukocytes, lymphocytes and red blood cells. A major impact on mature cell numbers may be seen particularly with neutrophils (neutropaenia) and platelets (thrombocytopenia), cells which naturally have relatively short half-lives. A decrease in leukocyte count, with concomitant loss of immune system function, may increase a patient's risk of opportunistic infection. Neutropaenia resulting from chemotherapy may for example occur within two or three days of cytotoxic treatments, end may leave the patient vulnerable to infection for up to 2 weeks until the hematopoietic system has recovered sufficiently to regenerate neutrophil counts. A reduced leukocyte count (leukopenia) and/or a platelet count (granulocytopenia) as a result of cancer therapy may become sufficiently serious that therapy must be interrupted to allow the white blood cell count to rebuild. Interruption of cancer therapy can in turn lead to survival of cancer cells, an increase in the incidence of drug resistance in cancer cells, and ultimately in cancer relapse. There is accordingly a need for therapeutic agents and treatments, which facilitate the preservation of hematopoietic progenitor or stem cells in patients subject to treatment with cytotoxic agents. There is similarly a need for therapeutic agents and treatments that facilitate the preservation or regeneration (self-renewal) of hematopoietic cell populations in cases where the number of such cells has been reduced due to disease or to therapeutic treatments such as radiation and chemotherapy.

Hematopoietic cells that are uncommitted to a final differentiated cell type are identified herein as "progenitor" cells. Hematopoietic progenitor cells possess the ability to differentiate into a final cell type directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage, as daughter cells become differentiated. The isolation of populations of mammalian bone marrow cell populations which are enriched to a greater or lesser extent in pluripotent stem cells has been reported (see for example, C. Verfaillie et al., J. Exp. Med., 172, 509 (1990), incorporated herein by reference).

Bone marrow transplantation has been used in the treatment of a variety of hematological, autoimmune and malignant diseases. In conjunction with bone marrow transplantation, ex vivo hematopoietic (bone marrow) cell culture may be used to expand the population of hematopoietic cells, particularly progenitor or stem cells, prior to reintroduction of such cells into a patient. In ex vivo gene therapy, hematopoietic cells may be transformed in vitro prior to reintroduction of the transformed cells into the patient. In gene therapy, using conventional recombinant DNA techniques, a selected nucliec acid, such as a gene, may be isolated, placed into a vector, such as a viral vector, and the vector transfected into a hematopoietic cell, to transform the cell, and the cell may in turn express the product coded for by the gene. The cell then may then be introduced into a patient. Hematopoietic stem cells were initially identified as a prospective target for gene therapy (see e.g., Wilson, J. M., et al., Proc. Natl. Acad. Sci 85: 3014-3018 (1988)). However, problems have been encountered in efficient hematopoietic stem cell transfection (see Miller, A. D., Blood 76: 271-278 (1990)). There is accordingly a need for agents and methods that facilitate the proliferation of hematopoietic cells in ex vivo cell culture. There is also a need for agents that may be used to facilitate the establishment and proliferation of engrafted hematopoietic cells that have been transplanted into a patient.

The broad application of hematopoietic stem cell transplantation therapy, however, may be limited by several features. The acquisition of enough stem cells for clinical use may require either a bone marrow harvest under general anesthesia or peripheral blood leukapheresis; both are expensive and carry a risk of morbidity. Grafts may contain only a limited number of useful hematopoietic progenitors. Additionally, the kinetics of short-term stem cell engraftment may be such that for the first 1-3 weeks after infusion, these cells offer little hematopoietic support, and therefor the recipients may remain profoundly myelosuppressed during this time.

Hematopoietic stem cells are reportedly found in peripheral blood of healthy persons. Their numbers however, may be insufficient to permit collection of an adequate graft by standard leukapheresis (Kessinger, A. et al., Bone Marrow Transplant 6, 643-646 (1989)). Fortunately, a variety of methods have been discovered to increase the circulation of progenitor and stem cells by "mobilizing" them from the marrow into the peripheral blood. For autologous transplantation, hematopoietic stem/progenitor cells may be mobilized into the peripheral blood (Lane T. A. Transfusion 36, 585-589 (1996)) during the rebound phase of the leukocytes after transient leukopenia induced by myelosuppressive chemotherapy, (Giralt S. et al., Blood, 89, 4531-4536 (1997) by hematopoietic growth factors, or (Lasky L. C. et al., Transfusion 21, 247-260 (1981)) by a combination of both.

Hematopoietic stem cell mobilization into peripheral blood has been used as a procedure following myelosuppressive chemotherapy regimens to mobilize hematopoietic stem and progenitor cells into the peripheral blood. Suggested treatment regimens for mobilization may include cyclophosphamide alone, in single doses of 4-7 g/m 2, or other agents such as Adriamycin (doxorubicin), carboplatin, Taxol (paclitaxel), etoposide, ifosfamide, daunorubicin, cytosine arabinosides 6-thioguanine, either alone or in combination (Richman, C. M. et al., Blood 47, 1031-1039 (1976); Stiff P. J. et al., Transfusion 23, 500-503 (1983); To L. B. et al. Bone Marrow Transplant 9, 277-284 (1992)). Such a regiment may induce a transient but profound myelosuppression in patients, with white blood cell (WBC) counts in some cases dropping below 100 cells-mm$^3$ 7-14 days after chemotherapy. This maybe followed on day 10-21 by rapid reappearance of leukocytes in the peripheral blood and frequently a "rebound" increase of the circulating leukocytes above baseline levels. As the leukocyte count rises, hematopoietic progenitor cells also begin to appear in the peripheral blood and rapidly increase.

Hematopoietic stem cells (HSC) collected from mobilized peripheral blood progenitor cells (PBPC) are increasingly used for both autologous and allogeneic transplantation after myeloablative or nonmyeloablative therapies (Lane T. A. Transfusion 36, 585-589 (1996)). Purported advantages of PBPC transplantation include rapid and durable trilineage hematologic engraftment, improved tolerance of the harvesting procedure (without general anesthesia), and possibly diminished tumor contamination in the autologous setting (Lasky L. C. et al., Transfusion 21, 247-260 (1981); Moss T. J. et al, Blood 76, 1879-1883)). Techniques for autologous mobilized PBPC grafting may also be successful for allogeneic transplantation. Early reports in animals and syngeneic transplants in humans supported this hypothesis (Kessionger, A. et al., Bone Marrow Transplant 6, 643-646 (1989)).

Many investigators have reported that PBPC mobilization employing a combination of chemotherapy and followed by growth factor (GM-CSF or G-CSF) administration is more effective than either chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Ho A. D. et al., Leukemia 7, 1738-1746 (1993)). The combination reportedly results in a 50- to 75-fold increase in circulating CFU-GM and 10- to 50-fold increase in $CD34^+$ cells (Pettengel R. et al., Blood, 2239-2248 (1993); Haas R. et al., Bone Marrow Transplant 9, 459-465 (1992); Ho A. D. et al., Leukemia 7, 1738-1746 (1993)). Direct comparisons show that chemotherapy and growth factors resulted in a mean 3.5-fold greater peak number of circulating CFU-GM (range, 0 to 6.8 times greater verses chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Moskowitz C. H. et al. Clin. Cancer Res. 4, 311-316 (1998)).

It is reportedly possible to expand hematopoietic progenitor cells in stroma-containing or nonstromal systems. Expansion systems have reportedly shown increases in CFU_GM of more than 100-fold. Enrichment of $CD34^+$ cells may be required before expansion in nonstromal culture but may not be necessary in stroma-containing systems. Early results of clinical trails are encouraging and have been taken to demonstrate that the engraftment potential of the expanded hematopoietic cells is not compromised by culture. Expansion of cord blood-derived hematopoietic cells may be especially important because of the limited number of cells that can be collected. Successful expansion of primitive and committed hematopoietic cells from cord blood may allow more extensive use in clinical transplantation, particularly in adult patients. Other possible applications of stem cell expansion include purging of tumor cells; production of immune-competent cells, such as dendritic cells and NK cells, and gene therapy.

Permanent marrow recovery after cytotoxic drug and radiation therapy generally depends on the survival of hematopoietic stem cells having long term reconstituting (LTR) potential. The major dose limiting sequelae consequent to chemotherapy and/or radiation therapy are typically neutropenia and thrombocytopenia. Protocols involving dose intensification (i.e., to increase the log-kill of the respective tumour therapy) or schedule compression may exacerbate the degree and duration of myelosuppression associated with the chemotherapy and/or radiation therapy. For instance, in the adjuvant setting, repeated cycles of doxorubicin-based treatment have been shown to produce cumulative and long-lasting damage in the bone marrow progenitor cell populations (Lorhrman et al., (1978) Br. J. Haematol. 40:369). The effects of short-term hematopoietic cell damage resulting from chemotherapy has been overcome to some extent by the concurrent use of G-CSF (Neupogen®), used to accelerate the regeneration of neutrophils (Le Chevalier (1994) Eur. J. Cancer 30A:410). This approach has been met with limitations also, as it may be accompanied by progressive thrombocytopenia and cumulative bone marrow damage as reflected by a reduction in the quality of mobilized progenitor cells over successive cycles of treatment. Because of the current interest in chemotherapy dose intensification as a means of improving tumour response rates and perhaps patient survival, the necessity for alternative therapies to either improve or replace current treatments to rescue the myeloablative effects of chemotherapy and/or radiation therapy has escalated, and is currently one of the major rate limiting factors for tumour therapy dose escalations.

Transplanted peripheral blood stem cells (PBSC, or autologous PBSC) may provide a rapid and sustained hematopoietic recovery after the administration of high-dose chemotherapy or radiation therapy in patients with hematological malignancies and solid tumours. PBSC transplantation has become the preferred source of stem cells for autologous transplantation because of the shorter time to engraftment and the lack of a need for surgical procedures such as are necessary for bone marrow harvesting (Demirer et al. (1996) Stem Cells 14:106-116; Pettengel et al., (1992) Blood 82:2239-2248). Although the mechanism of stem cell release into the peripheral blood from the bone marrow is not well understood, agents that augment the mobilization of $CD34^+$ cells may prove to be effective in enhancing autologous PBSC transplantation. G-CSF and GM-CSF are currently the most commonly used hematopoietic growth factors for PBSC mobilization, although the mobilized cellular profiles can differ significantly from patient to patient. Therefore, other agents are required for this clinical application.

It has been suggested that stem cell transplants for autoimmune disease should be initiated using autologous or allogenic grafts, where the former may be preferable since they may bear less risk of complication (Burt and Taylor (1999) Stem Cells 17:366-372). Lymphocyte depletion has also been recommended, where lymphocyte depletion is a form of purging autoreactive cells from the graft. In practice, aggressive lymphocyte depletion of an allograft can reportedly ameliorate autoreactivity (i.e., graft-versus-host disease (GVHD)) even without immunosuppressive prophylaxis. Therefore, a lymphocyte-depleted autograft may prevent recurrence of autoreactivity. As a consequence, any concurrent therapy that may enhance the survival of the CFU-GEMM myeloid stem cells, or BFU-E, CFUMeg (CFU-MK) and CFU-GM myelomonocytic stem cells may be beneficial in therapies for autoimmune diseases where hematopoietic stem cells could be compromised.

Platelet activation in healthy subjects after G-CSF administration has been reported. The effects were indicated by increased platelet expression of P-selectin (Avenarius H. J. et al., Int. J. Hematol. 58, 189-196 (1993), blood thromboxane B2, and AT-III complex levels R. G-CSF reportedly enhances platelet aggregation to collagen and adenosine diphosphate (Kuroiwa M. et al., Int. J. Hematol. 63, 311-316 (1996)). There have, however, been reports of arterial thrombosis in two patients with cancer who were receiving G-CSF after chemotherapy (Shimoda K. et al., J. Clin. Invest. 91, 1310-1313 (1993)), and concern has been expressed regarding induction of a possible prethrombotic state in some normal donors (Conti J. A. et al., Cancer 70, 2699-2707 (1992);

Kawachi Y. et al., Br. J. Haematol. 94, 413-416 (1996)) and such risk was suggested in two cases (Anderlini P. et al., Blood 90, 903-908 (1997)).

Depressed platelet count after PBPC collection may occur in healthy donors of allogeneic transplants. The decrease in platelet counts during apheresis for autologous transplant recipient can reportedly be substantial, especially for those heavily pretreated patients mobilized with chemotherapy plus growth factor. Platelet transfusion may be considered when the postapheresis count drops below 20.000/mm 3, although the threshold should be individualized and depends on the status of the patient (inpatient vs. outpatient), the history of platelet recovery after chemotherapy, the amount of infused anticoagulant (hence the number of prior apheresis sessions within the same mobilization and collection series), and whether apheresis will be performed the next day. It is possible to separate platelets from the PBPC product using a low-speed centrifugation procedure. The platelets may by infused fresh or cryopreserved for later infusion. (Schiffer C. A. et al., Ann N. Y. Acad. Sci. 411, 161-169 (1983)). The platelet cryopreservation procedure, however, has not been universally accepted. (Law P., Exp. Hematol. 10, 351-357 (1983)). Furthermore, the PBPC product of patients with a low platelet count and who require transfusion typically does not contain enough platelet to warrant processing (Lane, unpublished observation (Lane T. A. Transfusion 36, 585-589 (1996)).

Clinical trials using gene transfer into HSC have generally relied on retrovirus-mediated gene transfer methods. Retroviruses fill the need for stable and relatively efficient integration of engineered genetic elements into the chromosomes of target T cells. Other viral vector systems currently available, such as adenovirus or adenovirus-associated viral vectors, or transfection methods, such as lipofection, electroporation, calcium phosphate precipitation, or bioballistics, may lack similar efficiency for long-term expression of the transgenes in dividing HSC. Some vectors may not enter the cells in sufficient numbers without cytotoxicity and/or may not integrate stability into the chromosomes with useful efficiency. In dividing cells, unintegrated DNA is generally diluted and lost. Adenoviral vectors may also be highly immunogenic.

Retrovirus-mediated gene transfer into murine hematopoietic stem cells and reconstitution of syngeneic mice has demonstrated persistence and functioning of the transgenes over extended period of time (Kume et al. (1999) 69:227-233). Terminally differentiated cells are relatively short-lived, except for memory B and T lymphocytes, and a large number of blood cells are replaced daily. Therefore, when long-term functional correction of blood cells by gene transfer is required, the target cells may be hematopoietic stem cells (Kume et al. (1999) 69:227-233). Compounds that can maintain the survival and/or self-renewal (for example enhanced number of cells in S-phase of the cell cycle) of the progenitor stem cells may therefore increase the efficiency of the gene transfer in that a greater population of hematopoietic stems cells is available.

A number of proteins have been identified and may be utilized clinically as inhibitors of hematopoietic progenitor cell development and hematopoietic cell proliferation or multiplication. These include recombinant-methionyl human G-CSF (Neupogen®, Filgastim; Amgen), GM-CSF (Leukine®, Sargramostim; Immunex), erythropoietin (rhEPO, Epogene; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), stem cell factor (rhSCF, Stemgen®; Amgen).

BRIEF SUMMARY OF THE INVENTION

In accordance with various aspects of the invention, CXCR4 antagonists may be used to treat hematopoietic cells, for example to increase the rate of hematopoietic stem or progenitor cellular multiplication, self-renewal, expansion, proliferation, or peripheralization. In various aspects, the invention relates to methods of promoting the rate of hematopoietic cell multiplication, which encompases processes that increase and/or maintain cellular multiplication, self-renewal, expansion, proliferation or peripheralization. This may for example be useful in some embodiments for in vitro hematopoietic cell cultures used in bone marrow transplantation, peripheral blood mobilization, or ex vivo expansion. CXCR4 antagonists may also be used therapeutically to stimulate hematopoietic cell multiplication, self-renewal, expansion, proliferation or peripheralization in vivo, for example in some embodiments involving human diseases such as a cancer or an autoimmune disease. The hematopoietic cells targeted by the methods of the invention may include hematopoietic progenitor or stem cells.

In alternative embodiments, CXCR4 antagonists may be used to treat a variety of hematopoietic cells, and such cells may be isolated or may form only part of a treated cell population in vivo or in vitro. Cells amenable to treatment with CXCR4 antagonists may for example include cells in the hematopoietic lineage, beginning with pluripotent stem cells, such as bone marrow stem or progenitor cells, lymphoid stem or progenitor cells, myeloid stem cells, CFU-GEMM cells (colony-forming-unit granulocyte, erythroid, macrophage, megakaryocye), B stem cells, T stem cells, DC stem cells, pre-B cells, prothymocyte), BFU-E cells (burst-forming unit-erythroid), BFU-MK cells (burst-forming unit-megakaryocytes), CFU-GM cells (colony-forming unit-granulocyte-macrophage), CFU-bas cells (colony-forming unit-basophil), CFUMast cells (colony forming unit mast cell), CFU-G cells (colony forming unit granulocyte), CFU-M/DC cells (colony forming unit monocyte/dendritic cell), CFU-Eo cells (colony forming unit eosinophil), CFU-E cells (colony forming unit erythroid), CFU-MK cells (colony forming unit megakaryocyte), myeloblasts, monoblasts, B-lymphoblasts, T-lymphoblasts, proerythroblasts, neutrophillic myelocytes, promonocytes, or other hematopoietic cells that differentiate to give rise to mature cells such as macrophages, myeloid related dendritic cells, mast cells, plasma cells, erythrocytes, platelets, neutrophils, monocytes, eosinophils, basophils, B-cells, T-cells or lymphoid related dendritic cells.

In some embodiments, the invention provides methods of increasing the circulation of hematopoietic cells by mobilizing them from the marrow to the peripheral blood comprising administering an effective amount of a CXCR4 antagonist to hematopoietic cells of a patient undergoing autologous mobilization where hematopoietic stem/progenitor cells may be mobilized into the peripheral blood (1) during the rebound phase of the leukocytes and/or platelets after transient granulocytopenia and thrombocytopenia induced by myelosuppressive chemotherapy, (2) by hematopoietic growth factors, or (3) by a combination of both. Such treatment may for example be carried out so as to be effective to mobilize the hematopoietic cells from a marrow locus (i.e. a location in the bone marrow) to a peripheral blood locus (i.e. a location in the peripheral blood). Such treatments may for example be undertaken in the context of or for the clinical procedure of leukapheresis or apheresis. In alternative embodiments, CXCR4 antagonists may be used in ex vivo stem cell expansion to supplement stem cell grafts with more mature precursors to shorten or potentially prevent hematopoietic cell depletion, including conditions such as pancytopenia, granulocytopenia, thrombocytopenia, anemia or a combination thereof; to increase the number of primitive progenitors to help ensure hematopoietic support for multiple cycles of high-dose therapy; to obtain sufficient number of stem cells from a single marrow aspirate or apheresis procedure, thus reducing the need for large-scale harvesting of marrow of multiple leukopheresis; to generate sufficient cells from a single cord-blood unit to allow reconstitution in an adult after high-dose chemotherapy; to purge stem cell products of contaminating tumour cells; to generate large volumes of immunologically active cells with antitumour activity to be used in immunotherapeutic regimens or to increase the pool of stem cells that could be targets for the delivery of gene therapy.

In alternative embodiments, the invention provides methods to enrich CD34+progenitor cells which are utilized in bone marrow (BM) and peripheral blood (PB) stem cell transplantation, wherein the hematopoietic stem cell transplantation (HSCT) protocols may for example be utilized for the purpose of treating the following diseases (from Ball, E. D., Lister, J., and Law, P. Hematopoietic Stem Cell Therapy, Chruchill Livingston (of Harcourt Inc.), New York (2000)): Aplastic Anemia; Acute Lymphoblastic Anemia.; Acute Myelogenous Leukemia; Myelodysplasia; Multiple Myeloma; Chronic Lymphocytic Leukemia; Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency); Metabolic Diseases (for instance those which have been HSCT indicated such as Hurler Syndrome (MPS I/II), Sly NW Syndrome (MPS VII), Chilhood onset cerebral X-adrenoleukodystrophy, Globard_cell Leukodystrophy).

In some embodiments, peptide CXCR4 antagonists of the invention may comprise an N-terminal portion derived from SDF-1, covalently joined by a linker to a second N-terminal peptide, containing or now modifications to mimic N-terminal beta-turning, or C-terminal alpha-helices. The SDF-1 antagonist may also exist as an N-terminal Dimer.

DETAILED DESCRIPTION OF THE INVENTION

Figure 1:
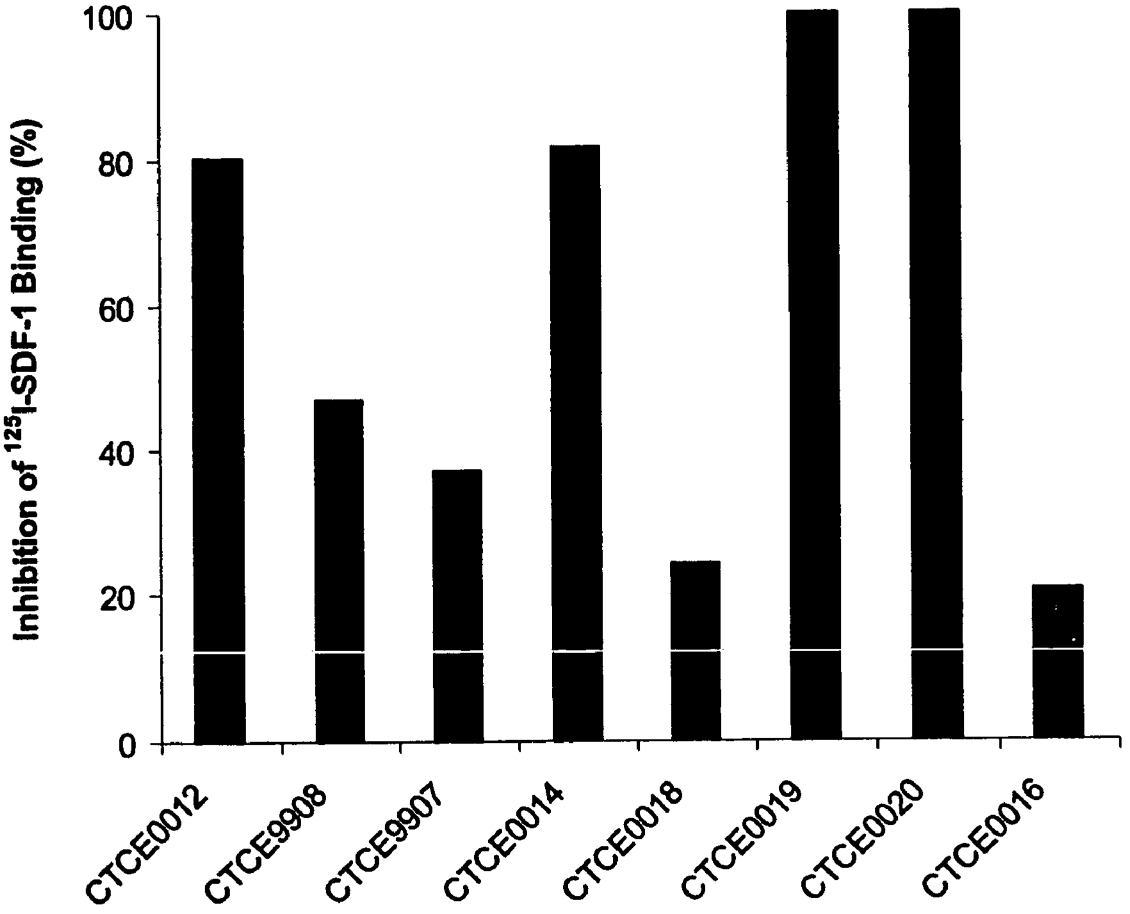
FIG. 1: shows the effects of CXCR4 receptor binding of SDF-1 peptide antagonists in an $^{125}$I-SDF-1 binding competition assay. Full length SDF-1 antagonist and the indicated analogs (competing ligands) were added to CEM cells in the presence of 4 nM $^{125}$I-SDF-1. CEM cells were assessed for $^{125}$I-SDF-1 binding following 2 hr incubation. The results are expressed as percentage of the maximal specific binding that was determined without competing ligand.

In one aspect, the invention provides uses for CXCR4 antagonists derived D from SDF-1 [P2G] in which glycine is substituted for proline at amino acid position 2. The full (67 amino acid long) versions of this analogue, designated SDF-1(1-67)[P2G], or SDF-1 [P2G] (SEQ ID NO:1), is a potent CXCR4 receptor antagonist (Crump et al., (1997) EMBO J. 16(23): 6996-7007). SDF-1 binds to CXCR4 primarily via its N-terminus, which appears flexible in the NMR studies of 5 active N-terminal peptides of SDF-1 (Elisseeva et al., J. Biol Chem (2000) 275(35) 26799-805). Residues 5-8, and to a less extent 11-14, form similar structures that can be characterized as a beta-turn of the beta-alpha R type. These structural motifs are likely to be interconverting with other states, but the major conformation may be important for recognition during receptor binding. The importance of beta-turns of peptides and proteins may well be crucial for receptor interactions that ultimately lead to biological activity. In recognition of this, there have been several efforts to 'lock' peptides and proteins into beta-turn configurations (Ripka, W. C. et al., Tetrahedron (1993) 49(17) 3593-3608 and Elseviers, M. et al., Biochem. Biophys. Res. Commun, (1988) 154-515). The natural amino-acid proline is known to a beta-turn inducer. In one aspect of this invention, versions of the full length antagonist analogues in which proline (P) was substituted into single position residues 5-8, designated SEQ ID NOS:2-5. In the same scheme, replacement of the natural amino acid proline by the so-called proline-amino acid chimera (P*) (Garland, R. M. Tetrahedron (1993) 49(17) 3547-3558 and Raman, S. et al., J. Org. Chem. (1996) 61(1) 202-208) in the full length antagonist gives rise to the designated analogues (SEQ ID NOS:6-9). Another mechanism of beta-turn induction/'locking' is the introduction of the Bicyclic Turned Dipeptide (Btd), as a beta-turn mimetic (Ukon Nagai et al Tetrahedron (1993) 49(17) 3577-3592) in the sequence of the full length antagonist as for proline and proline chimera. In this configuration, two successive amino acid are replaced at once by the Btd molecule, which when inserted into the SDF-1[P2G] antagonist are designated as SEQ ID NOS:10-12.

Sequences:

```
KGVSLSYRCPCRFFESHVARANVKHLKILNTPNCALQIVARLKNNNRQVCIDPKLKW  (SEQ ID NO:1)
IQEYLEKALN

KGVSPSYRCPCRFFESHVARANVKHLKILNTPNCALQIVARLKNNNRQVCIDPKLKW  (SEQ ID NO:2)
IQEYLEKALN
```

-continued

```
KGVSLPYRCPCRFFESHVARANVKHLKILNTPNCALQIVARLKNNNRQVCIDPKLKW (SEQ ID NO:3)
IQEYLEKALN

KGVSLSPRCPCRFFESHVARANVKHLKILNTPNCALQIVARLKNNNRQVCIDPKLKW (SEQ ID NO:4)
IQEYLEKALN

KGVSLSYPCPCRFFESHVARANVKHLKILNTPNCALQIVARLKNNNRQVCIDPKLKW (SEQ ID NO:5)
IQEYLEKALN

KGVSP*SYRCPCRFFESHVARANVKHLKILNTPNCALQIVARLKNNNRQVCIDPKLK (SEQ ID NO:6)
WIQEYLEKALN

KGVSLP*YRCPCRFFESHVARANVKHLKILNTPNCALQIVARLKNNNRQVCIDPKLK (SEQ ID NO:7)
WIQEYLEKALN

KGVSLSP*RCPCRFFESHVARANVKHLKILNTPNCALQIVARLKNNNRQVCIDPKLK (SEQ ID NO:8)
WIQEYLEKALN

KGVSLSYP*CPCRFFESHVARANVKHLKILNTPNCALQIVARLKNNNRQVCIDPKLK (SEQ ID NO:9)
WIQEYLEKALN

KGVSBtdYRCPCRFFESHVARANVKHLKILNTPNCALQIVARLKNNNRQVCIDPKLK (SEQ ID NO:10)
WIQEYLEKALN

KGVSLBtdRCPCRFFESHVARANVKHLKILNTPNCALQIVARLKNNNRQVCIDPKLK (SEQ ID NO:11)
WIQEYLEKALN

KGVSLSBtdCPCRFFESHVARANVKHLKILNTPNCALQIVARLKNNNRQVCIDPKLK (SEQ ID NO:12)
WIQEYLEKALN
Where P* =
```

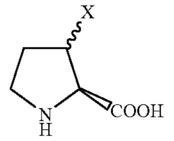

with X=Ar, Ar—OH, alkyl and more and Btd=

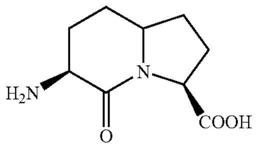

or

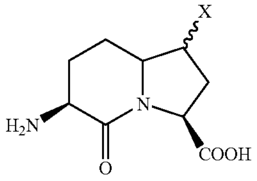

or

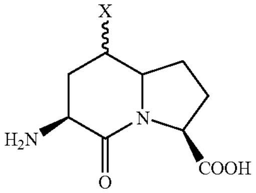

X = Alkyl, Ar, Ar—OH and more

A variety of small SDF-1 peptide analogues may also be used as CXCR4 antagonists, as disclosed in International Patent Publications WO 00/09152 (published 24 Feb 2000) and WO 99/47158 (published 23 Sep. 1999), each of which is incorporated herein by reference. One such peptide may be a monomer having the following sequences; KGVSLSYR-CPCRFFESH (SEQ ID NO:13); KGVSLSYRC (SEQ ID NO:14), or dimer of amino acids 1-9 (within SEQ ID NO:13), in which the amino acid chains are joined by a disulphide bond between each of the cysteines at position 9 in each sequence (designated SDF-1(1-9)$_2$[P2G] with the following sequence: KGVSLSYRC-CRYSLSVGK (SEQ ID NO:15)). Other An alternative peptides may for example be selected from the group consisting of peptides: KGVSLSYR-X-RYSLSVGK (SEQ ID NOS:16 and 17), that is a dimer of amino acids 1-8, in which the amino acid chains are joined by a linking moiety X (X may be an amino acid like lysine; ornithine or any other natural or unnatural amino acid serving as a linker between each of the arginines at position 8 in each sequence (designated SDF-1(1-8)$_2$[P2G]). Here again the notion of beta-turn mimetic was applied either for monomer (SEQ ID NO:13) in this case the following analogues were designated (SEQ ID NOS:18-28)

```
KGVSPSYRCPCRFFESH    (SEQ ID NO:18)
KGVSLPYRCPCRFFESH    (SEQ ID NO:19)
KGVSLSPRCPCRFFESH    (SEQ ID NO:20)
KGVSLSYPCPCRFFESH    (SEQ ID NO:21)
KGVSP*SYRCPCRFFESH   (SEQ ID NO:22)
KGVSLP*YRCPCRFFESH   (SEQ ID NO:23)
KGVSLSP*RCPCRFFESH   (SEQ ID NO:24)
KGVSLSYP*CPCRFFESH   (SEQ ID NO:25)
KGVSBtdYRCPCRFFESH   (SEQ ID NO:26)
KGVSLBtdRCPCRFFESH   (SEQ ID NO:27)
KGVSLSBtdCPCRFFESH   (SEQ ID NO:28)
```

Similar modifications may be made to monomeric peptides of the invention (SEQ ID NO:14)

```
KGVSPSYRC    (SEQ ID NO:29)
KGVSLPYRC    (SEQ ID NO:30)
```

-continued

| | |
|---|---|
| KGVSLS**P**RC | (SEQ ID NO:31) |
| KGVSLSY**P**C | (SEQ ID NO:32) |
| KGVS**P***SYRC | (SEQ ID NO:33) |
| KGVSL**P***YRC | (SEQ ID NO:34) |
| KGVSLS**P***RC | (SEQ ID NO:35) |
| KGVSLSY**P***C | (SEQ ID NO:36) |
| KGVS**Btd**YRC | (SEQ ID NO:37) |
| KGVSL**Btd**RC | (SEQ ID NO:38) |
| KGVSLS**Btd**C | (SEQ ID NO:39) |

Alternative peptides based on SEQ ID NO:15 are as follows, designated (SEQ ID NOS:40-50)

```
KGVSPSYRC   KGVSLPYRC   KGVSLSPRC   KGVSLSYPC
    |           |           |           |
KGVSPSYRC   KGVSLPYRC   KGVSLSPRC   KGVSLSYPC

KGVSP*SYRC  KGVSLP*YRC  KGVSLSP*RC  KGVSLSYP*C
    |           |           |           |
KGVSP*SYRC  KGVSLP*YRC  KGVSLSP*RC  KGVSLSYP*C

KGVSBtdYRC  KGVSLBtdRC  KGVSLSBtdC
    |           |           |
KGVSBtdYRC  KGVSLBtdRC  KGVSLSBtdC
```

In the same manner analogues based on the SEQ ID NO:16 are as follows, designated SEQ ID NOS:51-72).

```
KGVSPSYR   KGVSLPYR   KGVSLSPR   KGVSLSYP
    |          |          |          |
    X          X          X          X
    |          |          |          |
KGVSPSYR   KGVSLPYR   KGVSLSPR   KGVSLSYP

KGVSP*SYR  KGVSLP*YR  KGVSLSP*R  KGVSLSYP*
    |          |          |          |
    X          X          X          X
    |          |          |          |
KGVSP*SYR  KGVSLP*YR  KGVSLSP*R  KGVSLSYP*

KGVSBtdYR  KGVSLBtdR  KGVSLSBtd
    |          |          |
    X          X          X
    |          |          |
KGVSBtdYR  KGVSLBtdR  KGVSLSBtd
```

where X may be an amino acid like lysine; ornithine or any other natural or unnatural amino acid serving as a linker between each of the arginines at position 8 in each sequence.

In some embodiments, the CXCR4 antagonists for use in the invention may be substantially purified peptide fragments, modified peptide fragments, analogues or pharmacologically acceptable salts of either SDF-1α or SDF-1β. SDF-1 derived peptide antagonists of CXCR4 may be identified by known physiological assays and a variety of synthetic techniques (such as disclosed in Crump et al., 1997, The EMBO Journal 16(23) 6996-7007; and Heveker et al., 1998, Current Biology 8(7): 369-376; each of which are incorporated herein by reference). Such SDF-1 derived peptides may include homologs of native SDF-1, such as naturally occurring isoforms or genetic variants, or polypeptides having substantial sequence similarity to SDF-1, such as 20%, 30%, 40%, 50%, 60%, 70%, 80%, 90%, 95% or 99% sequence identity to at least a portion of the native SDF-1 sequence, the portion of native SDF-1 being any contiguous sequence of 10, 20, 30, 40, 50 or more amino acids, provided the peptides have CXCR4 antagonist activity. In some embodiments, chemically similar amino acids may be substituted for amino acids in the native SDF-1 sequence (to provide conservative amino acid substitutions). In some embodiments, peptides having an N-terminal LSY sequence motif within 10, or 7 amino acids of the N-terminus, and/or an N-terminal RFFESH (SEQ ID NO:73) sequence motif within 20 amino acids of the N-terminus may be used provided they have CXCR4 antagonistic activity. One family of such peptide antagonist candidates has an LSY motif at amino acids 5-7. Alternative peptides further include the RFFESH (SEQ ID NO:73) motif at amino acids 12-17. In alternative embodiments, the LSY motif is located at positions 3-5 of a peptide. The invention also provides peptide dimers having two amino acid sequences, which may each have the foregoing sequence elements, attached by a disulfide bridge within 20, or preferably within 10, amino acids of the N terminus, linking cysteine residues or α-aminobutric acid residues.

In other aspects, the invention relates to novel CXCR4 antagonists derived from SDF-1 [P2G] and their use to increase the rate of cellular multiplication and/or self-renweal of hematopoietic stem/progenitor cells. The antagonist compounds of the invention comprise an N-terminal portion of SDF-1 [P2G] covalently jointed by a linker to a second peptide. The N-terminal portion may be any portion of the SDF-1 [P2G] N-terminus which binds to CXCR4. The second peptide, which does not include an N-terminal portion of SDF-1 [P2G], preferably enhances the antagonistic effect of the compound and may be a C-terminal fragment of SDF-1, for example any C-terminal fragment of any chemokine that known to improve the activity by binding to GAG's (refer to Gabriele S. et al., Biochemistry (1999), 38: 12959-12968). SDF-1 Antagonists include an acid or amide peptide analog having SDF-1 [P2G] N terminal amino acids 1-14 or 1-17 linked to C-terminal residues 55-67 by a four glycine linker:

| | |
|---|---|
| KGVSLSYRCPCRFF-GGGG-LKWIQEYLEKALN | (SEQ ID NO:74) |
| KGVSLSYRCPCRFFESH-GGGG-LKWIQEYLEKALN | (SEQ ID NO:75) |

where the number of glycines linking the N-terminal and C-terminal amino acids may be varied, for example between 0 and 10, and may be 4, 3 or 2 in selected embodiments. The size of the linker may be adapted to correspond approximately to the distance between C-terminal and N-terminal regions in the native folded SDF-1 structure.

In other embodiments, a $(CH_2)_n$ linker may be used to join the N-terminal and C-terminal amino acids:

| | |
|---|---|
| KGVSLSYRCPCRFF-$(CH_2)_n$-LKWIQEYLEKALN | (SEQ ID NOS:76 and 77) |
| KGVSLSYRCPCRFFESH-$(CH_2)_n$-LKWIQEYLEKALN | (SEQ ID NOS:78 and 77) |

where n=1-20 or more. In such embodiments, the length of the linker may be adapted to correspond to the distance between the N- and C-terminal end of the full length SDF-1 [P2G] polypeptide in its native form (where the amino acids replaced by the corresponding linker are present).

The N-terminal LSYR (SEQ ID NO:140) residues which form a beta-turn (see Elisseeva et al., J. Bio. Chem. 275(35): 26799-26805) may be modified, similarly as the full length SDF 1 [P2G] anatagonist, for example, by substituting leucine (L); serine (S); tyrosine (Y) and arginine (R) with proline (P):

```
KGVSPSYRCPCRFF-GGGG-LKWIQEYLEKALN        (SEQ ID NO:79)
KGVSLPYRCPCRFF-GGGG-LKWIQEYLEKALN        (SEQ ID NO:80)
KGVSLSPRCPCRFF-GGGG-LKWIQEYLEKALN        (SEQ ID NO:81)
KGVSLSYPCPCRFF-GGGG-LKWIQEYLEKALN        (SEQ ID NO:82)
KGVSPSYRCPCRFFESH-GGGG-LKWIQEYLEKALN     (SEQ ID NO:83)
KGVSLPYRCPCRFFESH-GGGG-LKWIQEYLEKALN     (SEQ ID NO:84)
KGVSLSPRCPCRFFESH-GGGG-LKWIQEYLEKALN     (SEQ ID NO:85)
KGVSLSYPCPCRFFESH-GGGG-LKWIQEYLEKALN     (SEQ ID NO:86)
```

KGVSPSYRCPCRFF-$(CH_2)_n$-LKWIQEYLEKALN (SEQ ID NOS:87 and 77)

KGVSLPYRCPCRFF-$(CH_2)_n$-LKWIQEYLEKALN (SEQ ID NOS:88 and 77)

KGVSLSPRCPCRFF-$(CH_2)_n$-LKWIQEYLEKALN (SEQ ID NOS:89 and 77)

KGVSLSYPCPCRFF-$(CH_2)_n$-LKWIQEYLEKALN (SEQ ID NOS:90 and 77)

KGVSPSYRCPCRFFESH-$(CH_2)_n$-LKWIQEYLEKALN (SEQ ID NOS:91 and 77)

KGVSLPYRCPCRFFESH-$(CH_2)_n$-LKWIQEYLEKALN (SEQ ID NOS:92 and 77)

KGVSLSPRCPCRFFESH-$(CH_2)_n$-LKWIQEYLEKALN (SEQ ID NOS:93 and 77)

KGVSLSYPCPCRFFESH-$(CH_2)_n$-LKWIQEYLEKALN (SEQ ID NOS:94 and 77)

where the number of glycines or n (of $(CH_2)_n$) correspond to the length of the linker conferred to four glycines, or the distance between the N- and C-terminal end of the full length SDF-1 [P2G] polypeptide in its native form where the amino acids replaced by the corresponding linker are present.

In other embodiments, leucine (L), serine (S), tyrosine (Y) or arginine (R) may, be substituted with proline-amino acid chimera (P*) (similar to SEQ ID NOS:6-9 for the full length SDF-1 antagonist):

```
KGVSP*SYRCPCRFF-GGGG-LKWIQEYLEKALN       (SEQ ID NO:95)
KGVSLP*YRCPCRFF-GGGG-LKWIQEYLEKALN       (SEQ ID NO:96)
KGVSLSP*RCPCRFF-GGGG-LKWIQEYLEKALN       (SEQ ID NO:97)
KGVSLSYP*CPCRFF-GGGG-LKWIQEYLEKALN       (SEQ ID NO:98)
KGVSP*SYRCPCRFFESH-GGGG-LKWIQEYLEKALN    (SEQ ID NO:99)
```

-continued

```
KGVSLP*YRCPCRFFESH-GGGG-LKWIQEYLEKALN    (SEQ ID NO:100)
KGVSLSP*RCPCRFFESH-GGGG-LKWIQEYLEKALN    (SEQ ID NO:101)
KGVSLSYP*CPCRFFESH-GGGG-LKWIQEYLEKALN    (SEQ ID NO:102)
```

KGVSP*SYRCPCRFF-$(CH_2)_n$-LKWIQEYLEKALN (SEQ ID NOS:103 and 77)

KGVSLP*YRCPCRFF-$(CH_2)_n$-LKWIQEYLEKALN (SEQ ID NOS:104 and 77)

KGVSLSP*RCPCRFF-$(CH_2)_n$-LKWIQEYLEKALN (SEQ ID NOS:105 and 77)

KGVSLSYP*CPCRFF-$(CH_2)_n$-LKWIQEYLEKALN (SEQ ID NOS:106 and 77)

KGVSP*SYRCPCRFFESH-$(CH_2)_n$-LKWIQEYLEKALN (SEQ ID NOS:107 and 77)

KGVSLP*YRCPCRFFESH-$(CH_2)_n$-LKWIQEYLEKALN (SEQ ID NOS:108 and 77)

KGVSLSP*RCPCRFFESH-$(CH_2)_n$-LKWIQEYLEKALN (SEQ ID NOS:109 and 77)

KGVSLSYP*CPCRFFESH-$(CH_2)_n$-LKWIQEYLEKALN (SEQ ID NOS:110 and 77)

where the number of glycines or n (of $(CH_2)_n$) correspond to the length of the linker conferred to four glycines, or the distance between the N- and C-terminal end of the full length SDF-1 [P2G] polypeptide in its native form where the amino acids replaced by the corresponding linker are present.

In some embodiments, the peptidomimetics are of Btd (Bicyclo Turned Dipeptide) as described previously for the full length SDF-1 antagonist (SEQ ID NOS:77 and 111-122):

```
KGVSBtdYRCPCRFF-GGGG-LKWIQEYLEKALN       (SEQ ID NO:111)
KGVSLBtdRCPCRFF-GGGG-LKWIQEYLEKALN       (SEQ ID NO:112)
KGVSLSBtdCPCRFF-GGGG-LKWIQEYLEKALN       (SEQ ID NO:113)
KGVSBtdYRCPCRFFESH-GGGG-LKWIQEYLEKALN    (SEQ ID NO:114)
KGVSLBtdRCPCRFFESH-GGGG-LKWIQEYLEKALN    (SEQ ID NO:115)
KGVSLSBtdCPCRFFESH-GGGG-LKWIQEYLEKALN    (SEQ ID NO:116)
```

KGVSBtdYRCPCRFF-$(CH_2)_n$-LKWIQEYLEKALN (SEQ ID NOS:117 and 77)

KGVSLBtdRCPCRFF-$(CH_2)_n$-LKWIQEYLEKALN (SEQ ID NOS:118 and 77)

KGVSLSBtdCPCRFF-$(CH_2)_n$-LKWIQEYLEKALN (SEQ ID NOS:119 and 77)

KGVSBtdYRCPCRFFESH-$(CH_2)_n$-LKWIQEYLEKALN (SEQ ID NOS:120 and 77)

KGVSLBtdRCPCRFFESH-$(CH_2)_n$-LKWIQEYLEKALN (SEQ ID NOS:121 and 77)

-continued

KGVSLSBtdCPCRFFESH-$(CH_2)_n$- (SEQ ID NOS:122 and 77)
LKWIQEYLEKALN where the number of glycines or n (of $(CH_2)_n$) correspond to the length of the linker conferred to four glycines, or the distance between the N- and C-terminal end of the full length SDF-1 [P2G] polypeptide in its native form where the amino acids replaced by the corresponding linker are present.

The SDF-1-derived CXCR4 antagonists of the invention may be linear or cyclized. In some embodiments, the antagonists may be cyclized at glutamic acid at position 24 with lysine at position 20 or 28 by removing the allylic group from both side chains of lysine and glutamic acid using the palladium-(0) technique (as described in Kates et al., (1993) Anal. Biochem. 212, 303-310): 1-Allyl removal: A solution of tetrakis(triphenylphosphine)palladium(0) (3 fold excess) dissolved in 5% Acetic acid; 2.5% N-methylmorpholine (NMM) in chloroform under argon. The solution is added to the support-bound peptide previously removed from the column in a reaction vial containing a small magnetic bar for gentle stirring. The mixture is flushed with argon, sealed and stirred at room temperature for 6 hours. The support-bound peptide is transferred to a filter funnel, washed with a solution made of 0.5% sodium diethyldithiocarbamate in dichloromethane (DMF) and then dichloromethane. 2-Lactam formation is mediated by internal amide bond formation between the lysine and glutamic acid. Cyclisation is carried out manually in a peptide synthesis vial at room temperature overnight with gentle agitation. The coupling agent is 7-azabenzotriazol-1-yloxytris(pyrrolidino)phosphonium hexafluorophosphate (PyAOP)/N-methylmorpholine (NMM) (3 fold excess). (Jean-Rene Barbier et al., J. Med. Chem. (1997), 40: 1373-1380; ibid Biochemistry (2000), 39, 14522-14530). The following analogues were designated (SEQ ID NOS:123-126).

KGVSLSYRCPCRFFGGGGLKWIQEYLEKALN

KGVSLSYRCPCRFFESHGGGGLKWIQEYLEKALN

KGVSLSYRCPCRFFGGGGLKWIQEYLEKALN

KGVSLSYRCPCRFFESHGGGGLKWIQEYLEKALN

In some embodiments, glutamic acid (E) at position 24 and may be substituted with aspartic acid (D) and the aspartic acid cyclized with lysine at position 20 or 28 as described previously. In other embodiments, lysine at position 20 or 28 may be substituted with ornithine cyclized with either aspartic acid or glutamic acid at position 24 as described previously. This kind of substitution followed by cyclisation can be done with all analogues described above.

In other embodiments, lysine (K) at position 20 or 28 may be substituted with ornithine (O) and ornithine at position 20 or 28 cyclized with glutamic acid (or with substituted aspartic acid) at position 24 as described previously. Additionally, to form other cyclic rings, lysine may be substituted by leucine (L), or other hydrophpobic residues such as isoleucine (1), norleucine (Nle), valine (V), alanine (A), tryptophan (W), or phenylalanine (F). Lysine may also be substituted with methionine, however, methionine oxides and forms a disulphide bond making the peptide synthesis and purification more difficult.

CXCR4 antagonists of the present invention may further include hydrid analogs comprising N-terminal amino acid residues of SDF-1 [P2G] and amino acid residues of MIP-1α that are associated with GAG binding of the chemokine receptor, for example by replacing the relevant SDF-1 GAG-binding sequence, which may not be as specific as that of MIP-1α (see Gabriele S. et al., Biochemistry (1999) 38: 12959-12968 and Elisabeth M. et al., Virology (1999) 265, 354-364).

SDF-1[P2G](1-14)/MIP-1α(36-50) Hybrid Analog:
KGVSLSYRCPCRFF-GGGG- (SEQ ID NO:127)
SKPGVIFLTKRSRQV KGVSLSYRCPCRFF-$(CH_2)_n$- (SEQ ID NOS:128 and 129)
SKPGVIFLTKRSRQV SDF-1(1-14)/MIP-1α(55-70) Analog:
KGVSLSYRCPCRFF-GGGG- (SEQ ID NO:130)
EEWVQKYVDDLELSA KGVSLSYRCPCRFF-$(CH_2)_n$- (SEQ ID NO:131 and 132)
EEWVQKYVDDLELSA where the number of glycines or n (of $(CH_2)_n$) correspond to the length of the linker conferred to four glycines, or the distance between the N- and C-terminal end of the full length SDF-1 [P2G] polypeptide in its native form where the amino acids replaced by the corresponding linker are present.

It is well known in the art that some modifications and changes can be made in the structure of a polypeptide without substantially altering the biological function of that peptide, to obtain a biologically equivalent polypeptide. In one aspect of the invention, SDF-1 derived peptide antagonists of CXCR4 may include peptides that differ from a portion of the native SDF-1 sequence by conservative amino acid substitutions. The present invention also extends biologically equivalent peptides that differ from a portion of the sequence of novel antagonists of the present invention by conservative amino acid substitutions. As used herein, the term "conserved amino acid substitutions" refers to the substitution of one amino acid for another at a given location in the peptide, where the substitution can be made without loss of function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gin (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gin (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In some embodiments, CXCR4 antagonists are ligands that bind to CXCR4 with sufficient affinity and in such a manner so as to inhibit the effects of binding by an agonists, such as the natural ligand SDF-1, such as SDF-1-induced [Ca2+]i mobilization in cells. Example of CXCR4 antagonist assays may for example be found in International Patent Publications WO 00/09152 (published 24 Feb. 2000) and WO 99/47158 (published 23 Sep. 1999). In exemplary assays for CXCR4 antagonist activity, fura-2,AM loaded THP-1 cells may for example be incubated with putative antagonists, such as for 60 min prior to induction of [Ca2+]i mobilization by 10 nM SQF-1. Antagonists will typically demonstrate a dose responsive inhibition of SDF-1-induced [Ca2+]i mobilization.

Methods that may be utilized to determine whether a molecule functions as a CXCR4 antagonists include, but are not limited to, the following: Inhibition of the induction of SDF-1 receptor mediated rise in free cytosolic $Ca^{2+}$ concentration ($[Ca^{2+}]$) in response to native SDF-1 (or agonist analogs of SDF-1) (Loetscher P. et al., (1998) J. Biol. Chem. 273, 24966-24970), inhibition of SDF-1-induction of phosphoinositide-3 kinase or Protein Kinase C activity (Wang, J-F et al., (2000) Blood 95, 2505-2513), inhibition of SDF-1-induced migration of $CD34_+$ hematopoietic stem cells in a two-chamber migration (transwell) assay (Durig J. et al, (2000) Leukemia 14, 1652-1660; Peled A. et al., (2000) Blood 95, 3289-2396), inhibition of SDF-1 associated transmigration of $CD34^+$/$CXCR4^+$ cells through vascular endothelial cells in a cell chemotaxis assay, cell adhesion assay, or real-time tracking of $CD34^+$ cell migration in 3-D extracellular matrix-like gel assays (Peled A. et al., (2000) Blood 95, 3289-2396), inhibition of SDF-1 associated chemotaxis of marrow-derived B cell precursors (Nuzzo M. et al., Eur. J. Immunol. (1997) 27, 1788-1793), preventing CXCR4 signal transduction and coreceptor function in mediating the entry of T- and dual-tropic HIV isolates (Zhou N. et al., (2000) 39, 3782-3787), inhibition of SDF-1 associated increases of CFU-GM, CGU-M or BFU-E colony formation by peripheral blood $Inc^+$ $CD34^+$ progenitor cells (Lataillade J-J. et al/. (2000) Blood 95, 756-768), or inhibition of integrin-mediated adhesion of T cells to fibronectin and ICAM-1 (Buckley C. D et al., (2000) J. Immunology 165, 3423-3429). Where it is necessary to assess the inhibition of SDF-1 associated mechanisms in the aforementioned assays, various concentrations of CXCR4 antagonist may be incubated under the appropriate experimental conditions in the presence of SDF-1, in assays to determine if the CXCR4 antagonist associated repression of the respective mechanism results directly from inhibition of the CXCR4 receptor. ($[Ca^{2+}]$) mobilization, chemotaxis assays or other assays that measure the induction of CXCR4 are not limited to the cell types indicated in the associated references, but may include other cell types that demonstrate CXCR4 associated, and specific, activation.

In alternative aspects, the invention provides uses for CXCR4 antagonists that are identified as molecules that bind to CXCR4 (whether reversible or irreversible) and are associated with the repression of CXCR4 associated activity. Binding affinity of a CXCR4 antagonists may for example be associated with ligand binding assay dissociation constants ($K_D$) in the range of a minimum of 1 pM, 10 pM, 100 pM, 1 uM, 10 uM or 100 uM up to a maximum of 1 mM, or any value in any such range. CXCR4 antagonist associated $K_D$ values may be determined through alternative approaches, such as standard methods of radioligand binding assays, including High Throughput Fluorescence Polarization, scintillation proximity assays (SPA), and Flashplates™® (Allen et al., (2000) J. Biomolecular Screening 5, 63-69), where the competing ligand is native SDF-1. Alternatively, the affinity of a CXCR4 antagonist for the SDF-1 receptor (CXCR4) may be ascertained through inhibition of native SDF-1 binding to the CXCR4, where various concentrations of the CXCR4 antagonist are added in the presence of SDF-1 and a recombinant CXCR4 or a cell type that expresses an adequate receptor titer.

In alternative embodiments, the present invention relates to uses of small molecule non-peptide CXCR4 antagonists, such as a naphthoic acid derivative designated herein as 3-hydroxy-2-naphthoic acid (CAS 92-70-6; molecular formula:

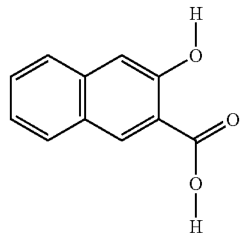

C11H803; molecular weight: 188.18):

In some embodiments, the invention provides pharmaceutical compositions containing CXCR4 antagonists. In one embodiment, such compositions include a CXCR4 antagonist compound in a therapeutically or prophylactically effective amount sufficient to alter bone marrow progenitor or stem cell growth, and a pharmaceutically acceptable carrier. In another embodiment, the composition includes a CXCR4 antagonist compound in a therapeutically or prophylactically effective amount sufficient to inhibit a cytotoxic effect of a cytotoxic agent, such as cytotoxic agents used in chemotherapy or radiation treatment of cancer, and a pharmaceutically acceptable carrier.

A "therapeutically effective amount" refers to an amount effective, at dosages and for periods of time necessary, to achieve the desired therapeutic result, such as reduction of bone marrow progenitor or stem cell multiplication, or reduction or inhibition of a cytotoxic effect of a cytotoxic agent. A therapeutically effective amount of CXCR4 antagonist may vary according to factors such as the disease state, age, sex, and weight of the individual, and the ability of the CXCR4 antagonist to elicit a desired response in the individual. Dosage regimens may be adjusted to provide the optimum therapeutic response. A therapeutically effective amount is also one in which any toxic or detrimental effects of the CXCR4 antagonist are outweighed by the therapeutically beneficial effects.

A "prophylactically effective amount" refers to an amount effective, at dosages and for periods of time necessary, to achieve the desired prophylactic result, such as preventing or inhibiting a cytotoxic effect of a cytotoxic agent. Typically, a prophylactic dose is used in subjects prior to or at an earlier stage of disease, so that a prophylactically effective amount may be less than a therapeutically effective amount.

In particular embodiments, a preferred range for therapeutically or prophylactically effective amounts of CXCR4 antagonists may be 0.1 nM-0.1 M, 0.1 nM-0.05 M, 0.05 nM-15 μM or 0.01 nM-100 μM. It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In some embodiments, CXCR4 agonists may be formulated in pharmaceutical compositions with additional active ingredients, or administered in methods of treatment in conjunction with treatment with one or more additional medications, such as a medicament selected from the following: recombinant-methionyl human. G-CSF (Neupogen®, Filgastim; Amgen), GM-CSF (Leukine®, Sargramostim; Immunex), erythropoietin (rhEPO, Epogen®; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), and stem cell factor (rhSCF, Stemgen®; Amgen).

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the CXCR4 antagonists may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a CXCR4 antagonist may be formulated with one or more additional compounds that enhance the solubility of the CXCR4 antagonist. The invention also extends to such derivatives of novel antagonists of the invention.

CXCR4 antagonist compounds of the invention may include SDF-1 derivatives, such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Ser-Ile-phenethylamide as an analogue of the tripeptide Ser-Ile-Phe). The invention also extends to such derivatives of the novel antagonists of the invention.

Within a CXCR4 antagonist compound of the invention, a peptidic structure (such as an SDF-1 derived peptide) maybe coupled directly or indirectly to at least one modifying group. Such modified peptides are also within the scope of the invention. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the SDF-1 core peptidic structure). For example, the modifying group can be coupled to the amino-terminus or carboxyterminus of an SDF-1 peptidic structure, or to a peptidic or peptidomimetic region flanking the core domain. Alternatively, the modifying group can be coupled to a side chain of at least one amino acid residue of a SDF-1 peptidic structure, or to a peptidic or peptido-mimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

In some embodiments, the modifying group may comprise a cyclic, heterocyclic or polycyclic group. The term "cyclic group", as used herein, includes cyclic saturated or unsaturated (i.e., aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups include pyrrolidine, oxolane, thiolane, imidazole, oxazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms are termed "bridged rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone ($C_1$-$C_{20}$ for straight chain, $C_3$-$C_{20}$ for branched chain), or 10 or fewer carbon atom. In some embodiments, cycloalkyls may have from 4-10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above:, but that contain at least one double or triple bond respectively.

The term "aralkyl", as used herein, refers to an alkyl or alkylenyl group substituted with at least one aryl group. Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —$N(R_\alpha)(R_\beta)$, in which $R_\alpha$ and $R_\beta$ are each independently hydrogen, alkyl, alkyenyl, alkynyl, aralkyl, aryl, or in which $R_\alpha$ and $R_\beta$ together with the nitrogen atom to which they are attached form a ring having 4-8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—$N(R_8)(R_9)$, in which $R_8$ and $R_9$ are as defined above. The term "acylamino" refers to —$N(R'_8)C(O)$—$R_7$, in which $R_7$ is as defined above and $R'_8$ is alkyl As used herein, the term "nitro" means —$NO_2$; the term "halogen" designates —F, —Cl, —Br or —I; the term "sulfhydryl" means —SH; and the term "hydroxyl" means-OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazoyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

Modifying groups may include groups comprising biotinyl structures, fluorescein-containing groups, a diethylene-triaminepentaacetyl group, a (−)-menthoxyacetyl group, a N-acetylneuraminyl group, a cholyl structure or an iminiobiotinyl group. A CXCR4 antagonist compound may be modified at its carboxy terminus with a cholyl group according to methods known in the art (see e.g., Wess, G. et al. (1993) Tetrahedron Letters, 34:817-822; Wess, G. et al. (1992) Tetrahedron Letters 33:195-198; and Kramer, W. et al. (1992) J. Biol. Chem. 267:18598-18604). Cholyl derivatives and analogues may also be used as modifying groups. For example, a preferred cholyl derivative is Aic (3-(O-aminoethyl-iso)-cholyl), which has a free amino group that can be used to further modify the CXCR4 antagonist compound. A modifying group may be a "biotinyl structure", which includes biotinyl groups and analogues and derivatives thereof (such as a 2-iminobiotinyl group). In another embodiment, the modifying group may comprise a "fluorescein-containing group", such as a group derived from reacting an SDF-1 derived peptidic structure with 5-(and 6-)-carboxyfluorescein, succinimidyl ester or fluorescein isothiocyanate. In various other embodiments, the modifying group(s) may comprise; an N-acetylneuraminyl group, a trans-4-cotininecarboxyl group, a 2-imino-1-imidazolidineacetyl group, an (S)-(−)-indoline-2-carboxyl group, a (−)-menthoxyacetyl group, a 2-norbornaneacetyl group, a oxo-5-acenaphthenebutyryl, a (−)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

A CXCR4 antagonist compound of the invention may be further modified to alter the specific properties of the compound while retaining the desired functionality of the compound. For example, in one embodiment, the compound may be modified to alter a pharmacokinetic property of the compound, such as in vivo stability, bioavailability or half-life. The compound may be modified to label the compound with a detectable substance. The compound may be modified to couple the compound to an additional therapeutic moiety. To further chemically modify the compound, such as to alter its pharmacokinetic properties, reactive groups can be derivatized. For example, when the modifying group is attached to the amino-terminal end of the SDF-1 core domain, the carboxy-terminal end of the compound may be further modified. Potential C-terminal modifications include those that reduce the ability of the compound to act as a substrate for carboxypeptidases. Examples of C-terminal modifiers include an amide group, an ethylamide group and various non-natural amino acids, such as D-amino acids and β-alanine. Alternatively, when the modifying group is attached to the carboxy-terminal end of the aggregation core domain, the amino-terminal end of the compound may be further modified, for example, to reduce the ability of the compound to act as a substrate for aminopeptidases.

A CXCR4 antagonist compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$. A CXCR4 antagonist compound may be radioactively labeled with $^{14}C$, either by incorporation of $^{14}C$ into the modifying group or one or more amino acid structures in the CXCR4 antagonist compound. Labeled CXCR4 antagonist compounds may be used to assess the in vivo pharmacokinetics of the compounds, as well as to detect disease progression or propensity of a subject to develop a disease, for example for diagnostic purposes. Tissue distribution CXCR4 receptors can be detected using a labeled CXCR4 antagonist compound either in vivo or in an in vitro sample derived from a subject. For use as an in vivo diagnostic agent, a CXCR4 antagonist compound of the invention may be labeled with radioactive technetium or iodine. A modifying group can be chosen that provides a site at which a chelation group for the label can be introduced, such as the Aic derivative of cholic acid, which has a free amino group. For example, a phenylalanine residue within the SDF-1 sequence (such as amino acid residue 13) may be substituted with radioactive iodotyrosyl. Any of the various isotopes of radioactive iodine may be incorporated to create a diagnostic agent. $^{123}I$ (half-life=13.2 hours) may be used for whole body scintigraphy, $^{124}I$ (half life=4 days) may be used for positron emission tomography (PET), $^{125}I$ (half life=60 days) may be used for metabolic turnover studies and $^{131}I$ (half life=8 days) may be used for whole body counting and delayed low resolution imaging studies.

In an alternative chemical modification, a CXCR4 antagonist compound of the invention may be prepared in a "prodrug" form, wherein the compound itself does not act as a CXCR4 antagonist, but rather is capable of being transformed, upon metabolism in vivo, into a CXCR4 antagonist compound as defined herein. For example, in this type of compound, the modifying group can be present in a prodrug form that is capable of being converted upon metabolism into the form of an active CXCR4 antagonist. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in Peptide-Based Drug Design: Controlling Transport and Metabolism, Taylor, M. D. and Amidon, G. L. (eds), Chapter 18.

CXCR4 antagonist compounds of the invention may be prepared by standard techniques known in the art. A peptide component of a CXCR4 antagonist may be composed, at least in part, of a peptide synthesized using standard techniques (such as those described in Bodansky, M. Principles of Peptide Synthesis, Springer Verlag, Berlin (1993); Grant, G. A. (ed.). Synthetic Peptides: A User's Guide, W. H. Freeman and Company, New York (1992); or Clark-Lewis, I., Dewald, B., Loetscher, M., Moser, B., and Baggiolini, M., (1994) J. Biol. Chem., 269, 16075-16081). Automated peptide synthesizers are commercially available (e.g., Advanced ChemTech Model 396; Milligen/Biosearch 9600). Peptides may be assayed for CXCR4 antagonist activity in accordance with standard methods. Peptides may be purified by HPLC and analyzed by mass spectrometry. Peptides may be dimerized via a disulfide bridge formed by gentle oxidation of the cysteines using 10% DMSO in water. Following HPLC purification dimer formation may be verified, by mass spectrometry. One or more modifying groups may be attached to a SDF-1 derived peptidic component by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)).

In another aspect of the invention, CXCR4 antagonist peptides may be prepared according to standard recombinant DNA techniques using a nucleic acid molecule encoding the peptide. A nucleotide sequence encoding the peptide may be determined using the genetic code and an oligonucleotide molecule having this nucleotide sequence may be synthesized by standard DNA synthesis methods (e.g., using an automated DNA synthesizer). Alternatively, a DNA molecule encoding a peptide compound may be derived from the natural precursor protein gene or cDNA (e.g., using the polymerase chain reaction (PCR) and/or restriction enzyme digestion) according to standard molecular biology techniques.

The invention also provides an isolated nucleic acid molecule comprising a nucleotide sequence encoding a peptide of the invention. In some embodiments, the peptide may comprise an amino acid sequence having at least one amino acid deletion compared to native SDF-1. The term "nucleic acid molecule" is intended to include DNA molecules and RNA molecules and may be single-stranded or double-stranded. In alternative embodiments, the isolated nucleic acid encodes a peptide ISM wherein one or more amino acids are deleted from the N-terminus, C-terminus and/or an internal site of SDF-1.

To facilitate expression of a peptide compound in a host cell by standard recombinant DNA techniques, the isolated nucleic acid encoding the peptide may be incorporated into a recombinant expression vector. Accordingly, the invention also provides recombinant expression vectors comprising the nucleic acid molecules of the invention. As used herein, the term "vector" refers to a nucleic acid molecule capable of transporting another nucleic acid to which it has been operatively linked. Vectors may include circular double stranded DNA plasmids, viral vectors. Certain vectors are capable of autonomous replication in a host cell into which they are introduced (such as bacterial vectors having a bacterial origin of replication and episomal mammalian vectors). Other vectors (such as non-episomal mammalian vectors) may be integrated into the genome of a host cell upon introduction into the host cell, and thereby may be replicated along with the host genome. Certain vectors may be capable of directing the expression of genes to which they are operatively linked. Such vectors are referred to herein as "recombinant expression vectors" or "expression vectors".

In recombinant expression vectors of the invention, the nucleotide sequence encoding a peptide may be operatively linked to one or more regulatory sequences, selected on the basis of the host cells to be used for expression. The terms "operatively linked" or "operably" linked mean that the sequences encoding the peptide are linked to the regulatory sequence(s) in a manner that allows for expression of the peptide compound. The term "regulatory sequence" includes promoters, enhancers, polyadenylation signals and other expression control elements. Such regulatory sequences are described, for example, in Goeddel; Gene Expression Technology: Methods in Enzymology 185, Academic Press, San Diego, Calif. (1990) (incorporated herein be reference). Regulatory sequences include those that direct constitutive expression of a nucleotide sequence in many types of host cell, those that direct expression of the nucleotide sequence only in certain host cells (such as tissue-specific regulatory sequences) and those that direct expression in a regulatable manner (such as only in the presence of an inducing agent). The design low of the expression vector may depend on such factors as the choice of the host cell to be transformed and the level of expression of peptide compound desired.

The recombinant expression vectors of the invention may be designed for expression of peptide compounds in prokaryotic or eukaryotic cells. For example, peptide compounds may be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector may be transcribed and translated in vitro, for example using T7 promoter regulatory sequences and T7 polymerase. Examples of vectors for expression in yeast *S. cerivisae* include pYepSec1 (Baldari et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Baculovirus vectors available for expression of proteins or peptides in cultured insect cells (e.g., Sf 9 cells) include the pAc series (Smith et al., (1983) Mol. Cell. Biol. 3:2156-2165) and the pVL series (Lucklow, V. A., and Summers, M. D., (1989) Virology 170:31-39). Examples of mammalian expression vectors include pCDM8 (Seed, B., (1987) Nature 329:840) and pMT2PC (Kaufman et al. (1987), EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40.

In addition to regulatory control sequences, recombinant expression vectors may contain additional nucleotide sequences, such as a selectable marker gene to identify host cells that have incorporated the vector. Selectable marker genes are well known in the art. To facilitate secretion of the peptide compound from a host cell, in particular mammalian host cells, the recombinant expression vector preferably encodes a signal sequence operatively linked to sequences encoding the amino-terminus of the peptide compound, such that upon expression, the peptide compound is synthesised with the signal sequence fused to its amino terminus. This signal sequence directs the peptide compound into the secretory pathway of the cell and is then cleaved, allowing for release of the mature peptide compound (i.e., the peptide compound without the signal sequence) from the host cell. Use of a signal sequence to facilitate secretion of proteins or peptides from mammalian host cells is well known in the art.

A recombinant expression vector comprising a nucleic acid encoding a peptide compound may be introduced into a host cell to produce the peptide compound in the host cell. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, a peptide compound may be expressed in bacterial cells such as *E. coli*, insect cells, yeast or mammalian cells. The peptide compound may be expressed in vivo in a subject to the subject by gene therapy (discussed further below).

Vector DNA can be introduced into prokaryotic or eukaryotic cells via conventional transformation, transfection or infection techniques. The terms "transformation", "transfection" or "infection" refer to techniques for introducing foreign nucleic acid into a host cell, including calcium phosphate or calcium chloride co-precipitation, DEAE-dextran-mediated transfection, lipofection, electroporation, microinjection and viral-mediated infection. Suitable methods for transforming, transfecting or infecting host cells can for example be found in Sambrook et al. (Molecular Cloning: A Laboratory Manual, 2nd Edition, Cold Spring Harbor Laboratory press (1989)), and other laboratory manuals. Methods for introducing DNA into mammalian cells in vivo are also known, and may be used to deliver the vector DNA of the invention to a subject for gene therapy.

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

A nucleic acid of the invention may be delivered to cells in vivo using methods such as direct injection of DNA, receptor-mediated DNA uptake or viral-mediated transfection. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263: 14621; Wilson et al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126).

Defective retroviruses are well characterized for use in gene transfer for gene therapy purposes (for reviews see Miller, A. D. (1990) Blood 76:271, Kume et al. (1999) International. J. Hematol. 69:227-233). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pL-J, pZIP, pWE and pEM, which are well known to those skilled in the art. Examples of suitable packaging virus lines include .pΨi.Crip, .pΨi.Cre, .pΨi.2, and .pΨi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc, Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application. WO 89/07136; PCT Application WO 89/02468; PCT Application WO 89/05345; and PCT Application WO 92/07573). In various embodiments, a genome of a retrovirus that encodes and expresses a polypeptide compound of the invention, may be utilized for the propagation and/or survival of cells, such as hematopoietic progenitor stem cells, for the purposes of maintaining and/or growing cells for the clinical purposes of blood transfusion or engraftment, host conditioning or applications relevant to chemotherapy, radiation therapy or myeloablative therapy.

For use. as a gene therapy vector, the genome of an adenovirus may be manipulated so that it encodes and expresses a peptide compound of the invention, but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad7, Adz etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482 6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). In various embodiments, a genome of an adenovirus that encodes and expresses a polypeptide compound of the invention, may be utilized for the propagation and/or survival of cells, such as hematopoietic progenitor stem cells, stromal cells, or mesenchymal cells, for the purposes of maintaining and/or growing cells for the clinical purposes of blood transfusion or engraftment, host conditioning or applications relevant to chemotherapy, radiation therapy or myeloablative therapy.

In some embodiments, adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al., (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be, used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). In some embodiments, a genome of an AAV that encodes and expresses a polypeptide compound of the invention, may be utilized for the propagation and/or survival of cells, such as hematopoietic progenitor stem cells, stromal cells or mesenchymal cells, for the purposes of maintaining and/or growing cells for the clinical purposes of blood transfusion or engraftment, host conditioning or applications relevant to chemotherapy, radiation therapy or myeloablative therapy.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods for grafting genetically modified cells to treat central nervous system disorders are described in U.S. Pat. No. 5,082,670 and in PCT Publications WO 90/06757 and WO 93/10234, all by Gage et al. Methods of gene transfer into hematopoietic cells have also previously been reported (see Clapp, D. W., et al., Blood 78: 1132-1139 (1991); Anderson, Science 288:627-9 (2000); and, Cavazzana-Calvo et al., Science 288:669-72 (2000), all of which are incorporated herein by reference).

Cancers susceptible to treatment with CXCR4 antagonists in accordance with various aspects of the invention may include both primary and metastatic tumors, such as solid tumors, including carcinomas of the breast, colon, rectum, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblast disease), male genital tract (including prostate, seminal vesicles, testes, and germ cell tumors), endocrine glands (including the thyroid, adrenal and pituitary glands), and skin, as well as hemangiomas, melanomas, sarcomas (including those arising from bone, and soft tissues as, well as Kaposi's sarcoma) and tumors of the brain, nerves, eyes, and meninges (including astrocytomas, gliomas, retinoblastomas, neuromas, neuroblastomas, Schwannomas, and meningiomas). In some aspects of the invention, CXCR4 antagonists may also serve in treating solid tumors arising from hematopoietic malignancies such as leukemias (i.e., chloromas, plasmacytomas and the plaques and tumors of mycosis fungoides and cutaneous T-cell lymphomalleukemia) as well as in the treatment of lymphoma (both Hodgkin's and non-Hodgkin's lymphomas). In addition, CDCR4 antagonists may be therapeutic in the prevention of metastasis from the tumors described above either when used alone or in combination with cytotoxic agents such as radiotherapy or chemotherapeutic agents (for instance refer to Zlotnik et al., Nature 410, 50-56, 2001).

In alternative aspects of the invention, CXCR4 antagonists such as SDF-1 polypeptides and non-peptide small molecule antagonists may target CD34+ cells to mediate release of CD34+ cells to the peripheral blood. In these aspects of the invention, CXCR4 antagonists may enhance circulating CD34+ cell proliferation and hematopoietic stem or progenitor cell survival or levels, which may for example be useful in stem cell transplantation or ex vivo expansion. Furthermore, CXCR4 antagonists may enhance hematopoietic stem or progenitor cell mobilization.

In various aspects of the invention, CXCR4 antagonists may be used in maintaining or augmenting the rate of hematopoietic cell multiplication. Method of the invention may comprise administration of an effective amount of CXCR4 antagonists to cells selected from the group consisting of hematopoietic stem cells and hematopoietic progenitor cells, stromal cells or mesenchymal cells. In alternative embodiments, a therapeutically effective amount of the CXCR4 antagonist may be administered to a patient in need of such treatment. Patients in need of such treatments may include, for example: patients having cancer, patients having an autoimmune disease, patients requiring functional gene transfer into hematopoietic stem cells, stromal cells or mesenchymal cells (such as for the dysfunction of any tissue or organ into which a stem cell may differentiate), patients requiring lymphocyte depletion, patients requiring depletion of a blood cancer in the form of purging autoreactive or cancerous cells using autologous or allgenic grafts, or patients requiring autologous peripheral blood stem cell transplantation. A patient in need of treatment in accordance with the invention may also be receiving cytotoxic treatments such as chemotherapy or radiation therapy. In some embodiments, CXCR4 antagonists may be used in treatment to purge an ex vivo hematopoietic stem cell culture of cancer cells with cytotoxic treatment, while preserving the viability and self-renewal of the hematopoietic progenitor or stem cells.

In alternative aspects the methods of treatment of the invention may be utilized where a patient is undergoing myelosuppressive treatment causing hematopoietic cell depletion, including pancytopenia, granulocytopenia, thrombocytopenia, anemia or a combination thereof. In further alternative embodiments, the patient to be treated may be suffering from AIDS, and the treatment may for example be effected to augment hematopoietic cell counts.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The disclosed uses for various embodiments are not necessarily obtained in all embodiments, and the invention may be adapted by those skilled in the art to obtain alternative utilities.

EXAMPLES

The following examples illustrate, but do not limit, the present invention.

Example 1

FIG. 1 shows the results of CXCR4 receptor binding assay. To obtain the results, antagonists (competing ligands) (20M) were added to 5×106 CEM cell/ml in the presence of 4 nM 125I-SDF-1. CEM cells were assessed for 125I-SDF-1 binding following 2 hr incubation. The results are expressed as percentages of the maximal specific binding in the absence of a competing ligand, and are the mean of three independent experiments. In FIG. 1, the antagonists tested were:

CTCE0012:
KGVSLSYRCPCRFFESHVARANVKHLKILNTPACALQIVARLKNNNRQVCIDPKLKW (SEQ ID NO:133)
IQEYLEKALN-COOH

CTCE9908:
$[KGVSLSYR]_2$-K-$CONH_2$ (SEQ ID NOS:134 and 135)

CTCE9907:
KGVSLSYRC($CONH_2$)-($CONH_2$)CRYSLSVGK (SEQ ID NO:136)

CTCE0014:
KGVSLSYRCPCRFF-GGGG-LKWIQEYLEKALN-COOH (SEQ ID NO:74)

CTCE0018:
KGVSLSYRCPCRFF-GGGG-LKWIQEYLEKALN-$CONH_2$ (SEQ ID NO:137)

CTCE0019:
KGVSLSYRCPCRFF-GGGG-LKWIQEYLEKALN-$CONH_2$ K20/E24 lactamization (SEQ ID NO:138)

CTCE0020:
KGVSLSYRCPCRFF-GGGG-LKWIQEYLEKALN-$CONH_2$ K28/E24 lactamization (SEQ ID NO:139)

CTCE0016:
KGVSLSYRCPCRFFESH-GGGG-LKWIQEYLEKALN-COOH (SEQ ID NO:75)

Example 2

Table 1 shows the effect of CXCR4 antagonists on hematopoietic cells, particularly primitive erythroide cells and primitive granulocytes (hematopoietic progenitor cells), compared to mature granulocytes. To obtain the data in Table 1, cells were pre-incubated with each of the compounds or saline alone (as control). The cells were then exposed to high dose $H^3$-thymidine, a cytotoxic agent. Rapidly dividing cells accumulate proportionally more of the cytotoxic radioactive thymidine and as a result are preferentially killed. The relative proportion of cells killed by the thymidine treatment compared to the control is indicative of the relative effectiveness of the compounds in increasing cellular multiplication, i.e. increasing the rate of cell cycle progression and DNA synthesis. A higher proportion of killed cells compared to the control is indicative that a compound increases cellular multiplication of the given cell type.

TABLE 1

Effect of CXCR4 Peptide Antagonists on the Cycling of Bone Marrow Progenitor Cells Exposed to $H^3$-Thymidine (% Cells Killed).

| Treatment | Dose (μg/ml) | % Kill After 3H-Thymidine BFU-E | CFU-GM |
|---|---|---|---|
| None | 10 | 3 +/− 2 | 3 +/− 3 |
| SDF-1(G2) | 10 | 48 +/− 5 | 38 +/− 4 |
| CTCE9907 | 50 | 39 +/ 7 | 28 +/− 6 |
| CTCE9908 | 50 | 51 +/− 7 | 36 +/− 6 |
| CTCE0012 | 10 | 60 +/− 8 | 44 +/− 4 |
| CTCE0016 | 10 | 63 +/− 5 | 54 +/− 4 |
| CTCE0017 | 50 | 57 +/− 3 | 52 +/− 6 |

In Table 1, SDF-1(G2) is the peptide KGVSLSYRCPCRFFESHVARANVKHLKILNTPACALQIVARLKNNNRQVCIDPKLKW IQEYLEKALN-COOH (SEQ ID NO:133), CTCE9907 is the peptide $[KGVSLSYRC-CONH_2]_2$ (SEQ ID NO:136), CTCE9908 is the peptide $[KGVSLSYR]_2$-K-$CONH_2$ (SEQ ID NOS:134 and 135), CTCE0012 is the peptide KGVSLSYRCPCRFFESHVARANVKHLKILNTPACALQIVARLKNNNRQVCIDPKLKW IQEYLEKALN-COOH (SEQ ID NO:133), CTCE0016 is the peptide KGVSLSYRCPCRFFESH-GGGG-LKWIQEYLEKALN-COOH (SEQ ID NO:75), and CTCE0017 is the peptide KGVSLSYRCPCRFF-GGGG-LKWIQEYLEKALN-$CONH_2$ (SEQ ID NO:137).

Example 3

Figure 2:
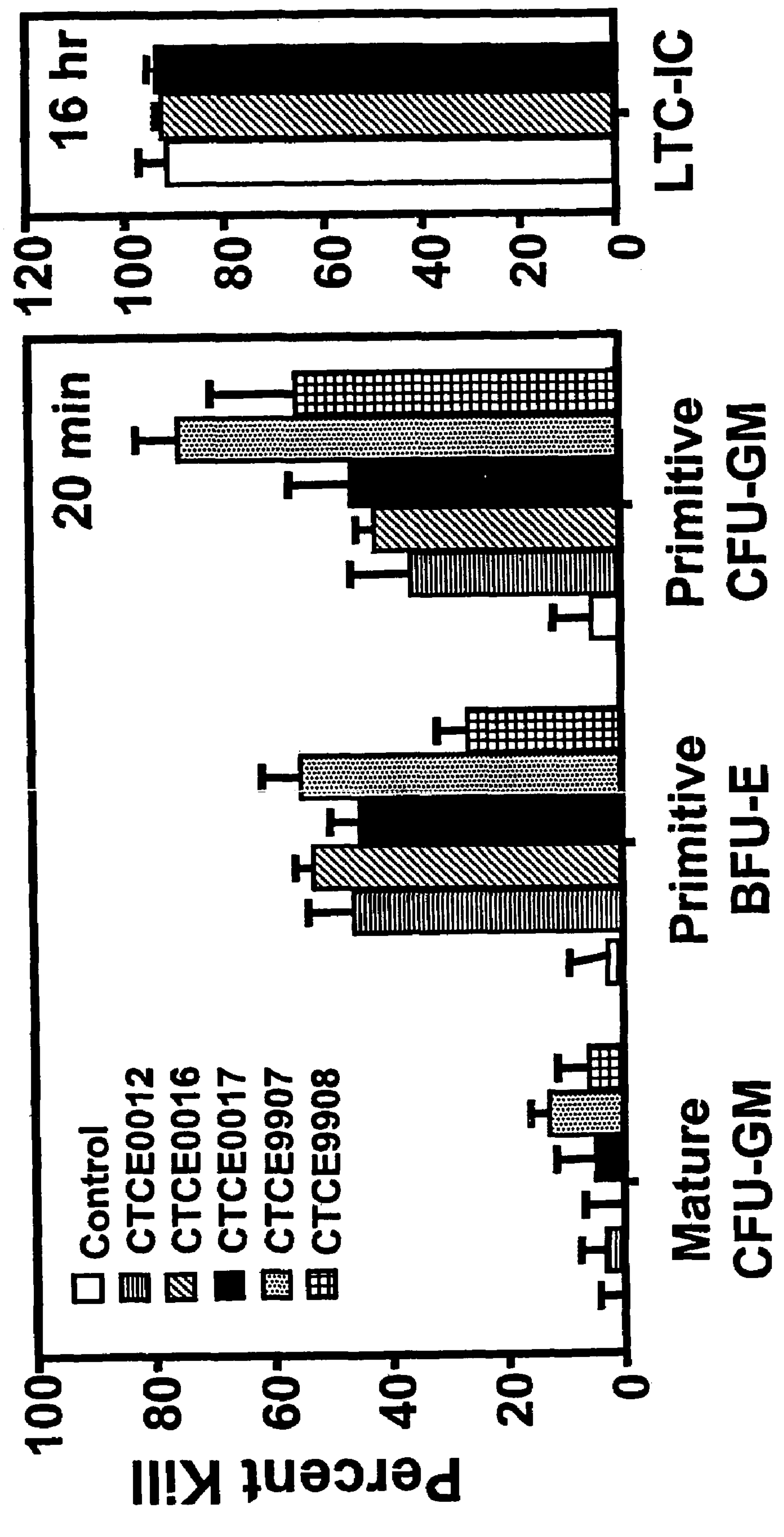
FIG. 2: shows the effect of SDF-1 peptide antagonists (defined in Examples) on the cycling of human progenitors from fetal liver transplanted NOD/SCID mice. The cycling status of mature and primitive colony forming cells (CFU-GM; colony forming unit-granulocyte-monocyte precursor, BFU-E; burst forming unit-erythroid precursor) in the suspension of $CD34^+$ cells isolated from the marrow of transplanted NOD/SCID mice was determined by assessing the proportion of these progenitors that were inactivated (killed) by short term (20 min) or overnight (LTC-1C long-term culture initiating cell) exposure of the cells to 20 μg/ml of high specific activity $^3$H-thymidine. Values represent the mean +/− the S.D. of data from up to four experiments with up to four mice per point in each. Since high specific activity $^3$H-thymidine affects proliferating cells, the higher degree in cell death resulting from SDF-1 antagonist incubation represents a significant enhancement in cell cycling (self-renewal).

FIG. 2 shows the efficacy of CXCR4 antagonists on enhancing the proliferation of human progenitor cells in an in vivo engraftment model.

In FIG. 2, the cycling status of mature and primitive colony forming cells (CFU-GM; colony forming unit-granulocyte-monocyte precursor, BFU-E; burst forming unit-erythroid precursor; LTC-IC, long-term culture initiating cell) in the suspension of $CD34^+$ cells isolated from the marrow of transplanted NOD/SCID mice was determined by assessing the proportion of these progenitors that were inactivated (killed) by short term (20 min) or overnight (16 hour) exposure of the cells to 20 μg/ml of high specific activity $^3$H-thymidine (values represent the mean +/− the S.D. of data from up to four experiments with up to four mice per point in each). Significant in the results is the observation that the SDF-1 peptide antagonists are effective at enhancing the proliferation of "primitive" human progenitor cells, as measured by the reduction of cells killed by exposure to high specific activity $^3$H-thymidine (which only affects proliferating cells).

In FIG. 2, the Control represents untreated cells, CTCE9907 is the peptide $[KGVSLSYRC-CONH_2]_2$ (SEQ ID NO:136), CTCE9908 is the peptide $[KGVSLSYR]_2$-K-$CONH_2$ (SEQ ID NOS:134 and 135), CTCE0012 is the peptide KGVSLSYRCPCRFFESHVARANVKHLKILNTPACALQIVARLKNNNRQVCIDPKLKW IQEYLEKALN-COOH (SEQ ID NO:133), CTCE0016 is the peptide KGVSLSYRCPCRFFESH-GGGG-LKWIQEYLEKALN-COOH (SEQ ID NO:75), and CTCE0017 is the peptide KGVSLSYRCPCRFF-GGGG-LKWIQEYLEKALN-$CONH_2$ (SEQ ID NO:137).

Example 4

Figure 3:
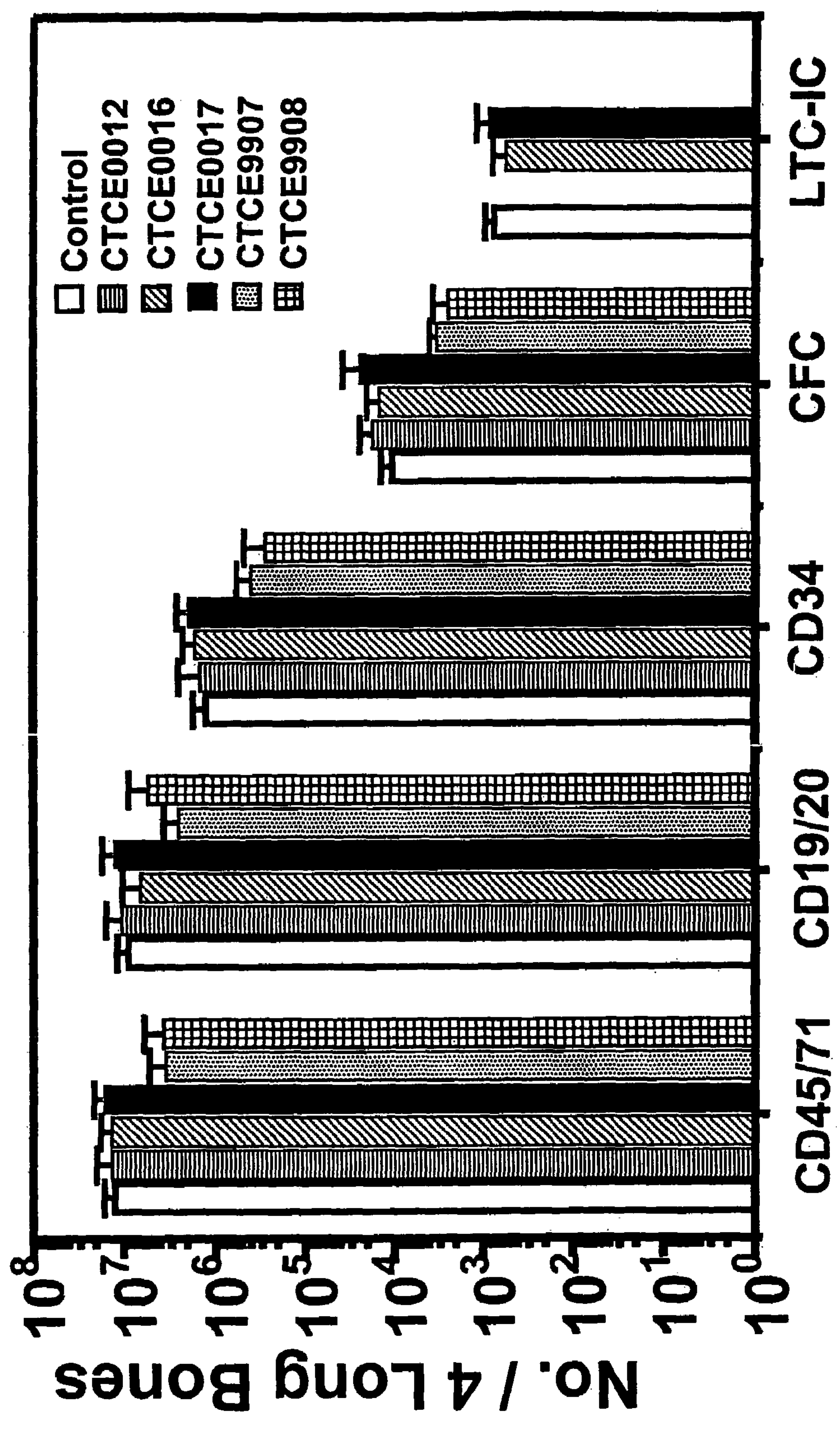
FIG. 3 shows the effect of SDF-1 peptide antagonists (defined in Examples) on the engraftment of human cells in human fetal liver transplanted NOD/SCID mice. A comparison of the number of phenotypically defined hematopoietic cells detected in the long bones (tibias and femurs) of mice four weeks after being transplanted with $10^7$ light-density human fetal liver blood cells and then administered with the indicated SDF-1 antagonists (0.5 mg/kg) three times per week for two weeks before sacrifice. Values represent the mean +/− one S.D. of results obtained from three to seven individual mice in three experiments.

FIG. 3. This example illustrates the effect of CXCR4 peptide antagonists on the engraftment of human cells in human fetal liver transplanted. NOD/SCID mice. The frequency of the phenotypically defined human hematopoietic cells detected in the long bones (tibias and femurs) of mice was determined. Administration of 0.5 mg/kg of SDF-1 had no significant effect on the number of CD45/71, CD19/20, or CD34 cells, nor on the CFC or LTC-IC. In addition, none of the human cell types were detectably affected by this schedule of CXCR4 agonist administration. This data indicates that SDF-1 peptide antagonists may effectively augment secondary engraftment of human progenitor cells, and that these compounds are essentially not toxic to the animals at the indicated doses.

In FIG. 3, the Control represents untreated cells, CTCE9907 is the peptide [KGVSLSYRC-$CONH_2$]$_2$ (SEQ ID NO:136), CTCE9908 is the peptide [KGVSLSYR]$_2$-K-$CONH_2$ (SEQ ID NOS:134 and 135), CTCE0012 is the peptide KGVSLSYRCPCRFFESHVARANVKHLKILNTPACALQIVARLKNNNRQVCIDPKLKWIQEYLEKALN-COOH (SEQ ID NO:133), CTCE0016 is the peptide KGVSLSYRCPCRFFESH-GGGG-LKWIQEYLEKALN-COOH (SEQ ID NO:75), and CTCE0017 is the peptide KGVSLSYRCPCRFF-GGGG-LKWIQEYLEKALN-$CONH_2$ (SEQ ID NO:137).

```
                     SEQUENCE LISTING

<160> NUMBER OF SEQ ID NOS: 140

<210> SEQ ID NO 1
<211> LENGTH: 67
<212> TYPE: PRT
<213> ORGANISM: Artificial Sequence
<220> FEATURE:
<223> OTHER INFORMATION: Description of Artificial Sequence:synthetic
      SDF-1(1-67)[P2G] CXCR4 receptor antagonist

<400> SEQUENCE: 1

Lys Gly Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
     50                  55                  60

Ala Leu Asn
 65


<210> SEQ ID NO 2
<211> LENGTH: 67
<212> TYPE: PRT
<213> ORGANISM: Artificial Sequence
<220> FEATURE:
<223> OTHER INFORMATION: Description of Artificial Sequence:synthetic
      SDF-1(1-67)[P2G] CXCR4 receptor antagonist
      analogue with proline (P) substituted at residue 5

<400> SEQUENCE: 2

Lys Gly Val Ser Pro Ser Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
     50                  55                  60

Ala Leu Asn
 65


<210> SEQ ID NO 3
<211> LENGTH: 67
<212> TYPE: PRT
<213> ORGANISM: Artificial Sequence
<220> FEATURE:
```

-continued

```
<223> OTHER INFORMATION: Description of Artificial Sequence:synthetic
      SDF-1(1-67)[P2G] CXCR4 receptor antagonist
      analogue with proline (P) substituted at residue 6

<400> SEQUENCE: 3

Lys Gly Val Ser Leu Pro Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65


<210> SEQ ID NO 4
<211> LENGTH: 67
<212> TYPE: PRT
<213> ORGANISM: Artificial Sequence
<220> FEATURE:
<223> OTHER INFORMATION: Description of Artificial Sequence:synthetic
      SDF-1(1-67)[P2G] CXCR4 receptor antagonist
      analogue with proline (P) substituted at residue 7

<400> SEQUENCE: 4

Lys Gly Val Ser Leu Ser Pro Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65


<210> SEQ ID NO 5
<211> LENGTH: 67
<212> TYPE: PRT
<213> ORGANISM: Artificial Sequence
<220> FEATURE:
<223> OTHER INFORMATION: Description of Artificial Sequence:synthetic
      SDF-1(1-67)[P2G] CXCR4 receptor antagonist
      analogue with proline (P) substituted at residue 8

<400> SEQUENCE: 5

Lys Gly Val Ser Leu Ser Tyr Pro Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65


<210> SEQ ID NO 6
<211> LENGTH: 67
<212> TYPE: PRT
```

-continued

<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 5
<220> FEATURE:
<221> NAME/KEY: MOD_RES
<222> LOCATION: (5)
<223> OTHER INFORMATION: Xaa = P* = proline-amino acid chimera
(3-aryl-proline, 3-hydroxyaryl-proline or 3-alkyl-proline)

<400> SEQUENCE: 6

Lys Gly Val Ser Xaa Ser Tyr Arg Cys Pro Cys Arg Phe Phe Glu Ser
1 5 10 15

His Val Ala Arg Ala Asn Val Lys His Leu Lys Ile Leu Asn Thr Pro
20 25 30

Asn Cys Ala Leu Gln Ile Val Ala Arg Leu Lys Asn Asn Asn Arg Gln
35 40 45

Val Cys Ile Asp Pro Lys Leu Lys Trp Ile Gln Glu Tyr Leu Glu Lys
50 55 60

Ala Leu Asn
65

<210> SEQ ID NO 7
<211> LENGTH: 67
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 6
<220> FEATURE:
<221> NAME/KEY: MOD_RES
<222> LOCATION: (6)
<223> OTHER INFORMATION: Xaa = P* = proline-amino acid chimera
(3-aryl-proline, 3-hydroxyaryl-proline or 3-alkyl-proline)

<400> SEQUENCE: 7

Lys Gly Val Ser Leu Xaa Tyr Arg Cys Pro Cys Arg Phe Phe Glu Ser
1 5 10 15

His Val Ala Arg Ala Asn Val Lys His Leu Lys Ile Leu Asn Thr Pro
20 25 30

Asn Cys Ala Leu Gln Ile Val Ala Arg Leu Lys Asn Asn Asn Arg Gln
35 40 45

Val Cys Ile Asp Pro Lys Leu Lys Trp Ile Gln Glu Tyr Leu Glu Lys
50 55 60

Ala Leu Asn
65

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 7
<220> FEATURE:
<221> NAME/KEY: MOD_RES
<222> LOCATION: (7)
<223> OTHER INFORMATION: Xaa = P* = proline-amino acid chimera
(3-aryl-proline, 3-hydroxyaryl-proline or 3-alkyl-proline)

<400> SEQUENCE: 8

-continued

```
Lys Gly Val Ser Leu Ser Xaa Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65
```

<210> SEQ ID NO 9
<211> LENGTH: 67
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue with proline-amino acid chimera (P*) substituted at residue 8
<220> FEATURE:
<221> NAME/KEY: MOD_RES
<222> LOCATION: (8)
<223> OTHER INFORMATION: Xaa = P* = proline-amino acid chimera (3-aryl-proline, 3-hydroxyaryl-proline or 3-alkyl-proline)

<400> SEQUENCE: 9

```
Lys Gly Val Ser Leu Ser Tyr Xaa Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
     50                  55                  60

Ala Leu Asn
 65
```

<210> SEQ ID NO 10
<211> LENGTH: 67
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue with Bicyclic Turned Dipeptide (Btd) substituted at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5-oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 10

```
Lys Gly Val Ser Xaa Xaa Tyr Arg Cys Pro Cys Arg Phe Phe Glu Ser
  1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45
```

-continued

Val Cys Ile Asp Pro Lys Leu Lys Trp Ile Gln Glu Tyr Leu Glu Lys
50 55 60

Ala Leu Asn
65

<210> SEQ ID NO 11
<211> LENGTH: 67
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue with Bicyclic Turned Dipeptide (Btd) substituted at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5-oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 11

Lys Gly Val Ser Leu Xaa Xaa Arg Cys Pro Cys Arg Phe Phe Glu Ser
1 5 10 15

His Val Ala Arg Ala Asn Val Lys His Leu Lys Ile Leu Asn Thr Pro
20 25 30

Asn Cys Ala Leu Gln Ile Val Ala Arg Leu Lys Asn Asn Asn Arg Gln
35 40 45

Val Cys Ile Asp Pro Lys Leu Lys Trp Ile Gln Glu Tyr Leu Glu Lys
50 55 60

Ala Leu Asn
65

<210> SEQ ID NO 12
<211> LENGTH: 67
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue with Bicyclic Turned Dipeptide (Btd) substituted at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5-oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 12

Lys Gly Val Ser Leu Ser Xaa Xaa Cys Pro Cys Arg Phe Phe Glu Ser
1 5 10 15

His Val Ala Arg Ala Asn Val Lys His Leu Lys Ile Leu Asn Thr Pro
20 25 30

Asn Cys Ala Leu Gln Ile Val Ala Arg Leu Lys Asn Asn Asn Arg Gln
35 40 45

Val Cys Ile Asp Pro Lys Leu Lys Trp Ile Gln Glu Tyr Leu Glu Lys
50 55 60

Ala Leu Asn

-continued

65

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue monomer

<400> SEQUENCE: 13

Lys Gly Val Ser Leu Ser Tyr Arg Cys Pro Cys Arg Phe Phe Glu Ser
1 5 10 15

His

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue monomer

<400> SEQUENCE: 14

Lys Gly Val Ser Leu Ser Tyr Arg Cys
1 5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer
<220> FEATURE:
<221> NAME/KEY: MOD_RES
<222> LOCATION: (9)
<223> OTHER INFORMATION: Xaa = Cys disulphide linked to the Cys at
position 9 of KGVSPSYRC (SEQ ID NO:15)
<220> FEATURE:
<221> NAME/KEY: DISULFID
<222> LOCATION: (9)
<223> OTHER INFORMATION: dimer of amino acids 1-9 in which the amino
acid chains are joined by a disulphide bond between
each of the cysteines at position 9 in each sequence

<400> SEQUENCE: 15

Lys Gly Val Ser Leu Ser Tyr Arg Xaa
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer
<220> FEATURE:
<221> NAME/KEY: MOD_RES
<222> LOCATION: (9)
<223> OTHER INFORMATION: Xaa = an amino acid like Lys, ornithine or any
other natural or unnatural amino acid serving as a
linker to the Arg at position 8 of KGVSLSYR
(SEQ ID NO:17)

<400> SEQUENCE: 16

Lys Gly Val Ser Leu Ser Tyr Arg Xaa
1 5

-continued

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer
<220> FEATURE:
<221> NAME/KEY: MOD_RES
<222> LOCATION: (8)
<223> OTHER INFORMATION: Xaa = Arg linked with Xaa at position 9 of KGVSLSYRX (SEQ ID NO:16)

<400> SEQUENCE: 17

```
Lys Gly Val Ser Leu Ser Tyr Xaa
  1               5
```

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue monomer

<400> SEQUENCE: 18

```
Lys Gly Val Ser Pro Ser Tyr Arg Cys Pro Cys Arg Phe Phe Glu Ser
  1               5                  10                  15

His
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue monomer

<400> SEQUENCE: 19

```
Lys Gly Val Ser Leu Pro Tyr Arg Cys Pro Cys Arg Phe Phe Glu Ser
  1               5                  10                  15

His
```

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue monomer

<400> SEQUENCE: 20

```
Lys Gly Val Ser Leu Ser Pro Arg Cys Pro Cys Arg Phe Phe Glu Ser
  1               5                  10                  15

His
```

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue monomer

<400> SEQUENCE: 21

```
Lys Gly Val Ser Leu Ser Tyr Pro Cys Pro Cys Arg Phe Phe Glu Ser
  1               5                  10                  15
```

-continued

His

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 5
<220> FEATURE:
<221> NAME/KEY: MOD_RES
<222> LOCATION: (5)
<223> OTHER INFORMATION: Xaa = P* = proline-amino acid chimera
(3-aryl-proline,3-hydroxyaryl-proline or 3-alkyl-proline)

<400> SEQUENCE: 22

Lys Gly Val Ser Xaa Ser Tyr Arg Cys Pro Cys Arg Phe Phe Glu Ser
1 5 10 15

His

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 6
<220> FEATURE:
<221> NAME/KEY: MOD_RES
<222> LOCATION: (6)
<223> OTHER INFORMATION: Xaa = P* = proline-amino acid chimera
(3-aryl-proline, 3-hydroxyaryl-proline or 3-alkyl-proline)

<400> SEQUENCE: 23

Lys Gly Val Ser Leu Xaa Tyr Arg Cys Pro Cys Arg Phe Phe Glu Ser
1 5 10 15

His

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with proline-amino acid chimera (P*) substituted
at residue 7
<220> FEATURE:
<221> NAME/KEY: MOD_RES
<222> LOCATION: (7)
<223> OTHER INFORMATION: Xaa = P* = proline-amino acid chimera
(3-aryl-proline,3-hydroxyaryl-proline or 3-alkyl-proline)

<400> SEQUENCE: 24

Lys Gly Val Ser Leu Ser Xaa Arg Cys Pro Cys Arg Phe Phe Glu Ser
1 5 10 15

His

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence:synthetic -continued

```
      SDF-1[P2G] CXCR4 receptor antagonist analogue
      with proline-amino acid chimera (P*) substituted
      at residue 8
<220> FEATURE:
<221> NAME/KEY: MOD_RES
<222> LOCATION: (8)
<223> OTHER INFORMATION: Xaa = P* = proline-amino acid chimera
      (3-aryl-proline,3-hydroxyaryl-proline or 3-alkyl-proline)

<400> SEQUENCE: 25

Lys Gly Val Ser Leu Ser Tyr Xaa Cys Pro Cys Arg Phe Phe Glu Ser
  1               5                  10                  15

His


<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with Bicyclic Turned Dipeptide (Btd) substituted
      at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5-oxo-6-amino-2,7,8,9-
      tetrahydro-indolizine or 3-carboxy-5-oxo-6-amino-[8-
      alkyl/aryl/hydroxyaryl]-1,2,7,9-tetrahydro-indolizine) single
      residue

<400> SEQUENCE: 26

Lys Gly Val Ser Xaa Xaa Tyr Arg Cys Pro Cys Arg Phe Phe Glu Ser
  1               5                  10                  15

His


<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with Bicyclic Turned Dipeptide (Btd) substituted
      at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5-oxo-6-amino-2,7,8,9-
      tetrahydro-indolizine or 3-carboxy-5-oxo-6-amino-[8-
      alkyl/aryl/hydroxyaryl]-1,2,7,9-tetrahydro-indolizine) single
      residue

<400> SEQUENCE: 27

Lys Gly Val Ser Leu Xaa Xaa Arg Cys Pro Cys Arg Phe Phe Glu Ser
  1               5                  10                  15

His


<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with Bicyclic Turned Dipeptide (Btd) substituted
```

-continued

```
      at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5-oxo-6-amino-2,7,8,9-
      tetrahydro-indolizine or 3-carboxy-5-oxo-6-amino-[8-
      alkyl/aryl/hydroxyaryl]-1,2,7,9-tetrahydro-indo
      lizine)

<400> SEQUENCE: 28

Lys Gly Val Ser Leu Ser Xaa Xaa Cys Pro Cys Arg Phe Phe Glu Ser
  1               5                  10                  15

His


<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue monomer

<400> SEQUENCE: 29

Lys Gly Val Ser Pro Ser Tyr Arg Cys
  1               5


<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue monomer

<400> SEQUENCE: 30

Lys Gly Val Ser Leu Pro Tyr Arg Cys
  1               5


<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue monomer

<400> SEQUENCE: 31

Lys Gly Val Ser Leu Ser Pro Arg Cys
  1               5


<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue monomer

<400> SEQUENCE: 32

Lys Gly Val Ser Leu Ser Tyr Pro Cys
  1               5


<210> SEQ ID NO 33
<211> LENGTH: 9
<212> TYPE: PRT
<213> ORGANISM: Artificial Sequence
```

-continued

```
<220> FEATURE:
<223> OTHER INFORMATION: Description of Artificial Sequence:synthetic
      SDF-1[P2G] CXCR4 receptor antagonist analogue
      with proline-amino acid chimera (P*) substituted
      at residue 5
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)

<400> SEQUENCE: 33

Lys Gly Val Ser Xaa Ser Tyr Arg Cys
  1               5


<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with proline-amino acid chimera (P*) substituted
      at residue 6
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)

<400> SEQUENCE: 34

Lys Gly Val Ser Leu Xaa Tyr Arg Cys
  1               5


<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with proline-amino acid chimera (P*) substituted
      at residue 7
<220> FEATURE:
<221> NAME/KEY: MOD_RES
<222> LOCATION: (7)
<223> OTHER INFORMATION: Xaa = P* = proline-amino acid chimera
      (3-aryl-proline,3-hydroxyaryl-proline or 3-alkyl-proline)

<400> SEQUENCE: 35

Lys Gly Val Ser Leu Ser Xaa Arg Cys
  1               5


<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue
      with proline-amino acid chimera (P*) substituted
      at residue 8
<220> FEATURE:
<221> NAME/KEY: MOD_RES
<222> LOCATION: (8)
<223> OTHER INFORMATION: Xaa = P* = proline-amino acid chimera
      (3-aryl-proline,3-hydroxyaryl-proline or 3-alkyl-proline)

<400> SEQUENCE: 36

Lys Gly Val Ser Leu Ser Tyr Xaa Cys
  1               5
```

-continued

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with Bicyclic Turned Dipeptide (Btd) substituted
at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 37

```
Lys Gly Val Ser Xaa Xaa Tyr Arg Cys
  1               5
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with Bicyclic Turned Dipeptide (Btd) substituted
at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 38

```
Lys Gly Val Ser Leu Xaa Xaa Arg Cys
  1               5
```

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue
with Bicyclic Turned Dipeptide (Btd) substituted
at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 39

```
Lys Gly Val Ser Leu Ser Xaa Xaa Cys
  1               5
```

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence:synthetic -continued

```
      SDF-1 CXCR4 receptor antagonist analogue dimer
<220> FEATURE:
<221> NAME/KEY: MOD_RES
<222> LOCATION: (9)
<223> OTHER INFORMATION: Xaa = Cys disulphide linked to the Cys at
      position 9 of KGVSPSYRC (SEQ ID NO:40)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 40

Lys Gly Val Ser Pro Ser Tyr Arg Xaa
  1               5


<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = Cys disulphide linked to the Cys at
      position 9 of KGVSLPYRC (SEQ ID NO:41)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 41

Lys Gly Val Ser Leu Pro Tyr Arg Xaa
  1               5


<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = Cys disulphide linked to the Cys at
      position 9 of KGVSLSPRC (SEQ ID NO:42)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 42

Lys Gly Val Ser Leu Ser Pro Arg Xaa
  1               5


<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
```

-continued

```
<220> FEATURE:
<221> NAME/KEY: MOD_RES
<222> LOCATION: (9)
<223> OTHER INFORMATION: Xaa = Cys disulphide linked to the Cys at
      position 9 of KGVSLSYPC (SEQ ID NO:43)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 43

Lys Gly Val Ser Leu Ser Tyr Pro Xaa
  1               5


<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 5 of each monomer sequence
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = Cys disulphide linked to the Cys at
      position 9 of KGVSP*SYRC (SEQ ID NO:44)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 44

Lys Gly Val Ser Xaa Ser Tyr Arg Xaa
  1               5


<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 6 of each monomer sequence
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = Cys disulphide linked to the Cys at
      position 9 of KGVSLP*YRC (SEQ ID NO:45)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence
```

-continued

<400> SEQUENCE: 45

Lys Gly Val Ser Leu Xaa Tyr Arg Xaa
1 5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with proline-amino acid chimera (P*) substituted at residue 7 of each monomer sequence
<220> FEATURE:
<221> NAME/KEY: MOD_RES
<222> LOCATION: (7)
<223> OTHER INFORMATION: Xaa = P* = proline-amino acid chimera (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = Cys disulphide linked to the Cys at position 9 of KGVSLSP*RC (SEQ ID NO:46)
<220> FEATURE:
<221> NAME/KEY: DISULFID
<222> LOCATION: (9)
<223> OTHER INFORMATION: dimer of amino acids 1-9 in which the amino acid chains are joined by a disulphide bond between each of the cysteines at position 9 in each sequence

<400> SEQUENCE: 46

Lys Gly Val Ser Leu Ser Xaa Arg Xaa
1 5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with proline-amino acid chimera (P*) substituted at residue 8 of each monomer sequence
<220> FEATURE:
<221> NAME/KEY: MOD_RES
<222> LOCATION: (8)
<223> OTHER INFORMATION: Xaa = P* = proline-amino acid chimera (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = Cys disulphide linked to the Cys at position 9 of KGVSLSYP*C (SEQ ID NO:47)
<220> FEATURE:
<221> NAME/KEY: DISULFID
<222> LOCATION: (9)
<223> OTHER INFORMATION: dimer of amino acids 1-9 in which the amino acid chains are joined by a disulphide bond between each of the cysteines at position 9 in each sequence

<400> SEQUENCE: 47

Lys Gly Val Ser Leu Ser Tyr Xaa Xaa
1 5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer -continued

```
      with Bicyclic Turned Dipeptide (Btd) substituted
      at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (9)
<223> OTHER INFORMATION: Xaa = Cys disulphide linked to the Cys at
      position 9 of KGVSBtdYRC (SEQ ID NO:48)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 48

Lys Gly Val Ser Xaa Xaa Tyr Arg Xaa
  1               5


<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (9)
<223> OTHER INFORMATION: Xaa = Cys disulphide linked to the Cys at
      position 9 of KGVSLBtdRC (SEQ ID NO:49)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 9 in each
      sequence

<400> SEQUENCE: 49

Lys Gly Val Ser Leu Xaa Xaa Arg Xaa
  1               5


<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide
      (3-carboxy-5-oxo-6-amino-1,2,7,8,9-pentahydro-indolizine,
```

-continued

[1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (9)
<223> OTHER INFORMATION: Xaa = Cys disulphide linked to the Cys at
      position 9 of KGVSLSBtdC (SEQ ID NO:50)
<220> FEATURE:
<221> NAME/KEY: DISULFID
<222> LOCATION: (9)
<223> OTHER INFORMATION: dimer of amino acids 1-9 in which the amino
      acid chains are joined by a disulphide bond between
      each of the cysteines at position 8 in each
      sequence

<400> SEQUENCE: 50

Lys Gly Val Ser Leu Ser Xaa Xaa Xaa
  1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSPSYR
      (SEQ ID NO:52)

<400> SEQUENCE: 51

Lys Gly Val Ser Pro Ser Tyr Arg Xaa
  1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (8)
<223> OTHER INFORMATION: Xaa = Arg linked with Xaa at position 9 of
      KGVSPSYRX (SEQ ID NO:51)

<400> SEQUENCE: 52

Lys Gly Val Ser Pro Ser Tyr Xaa
  1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSLPYR
      (SEQ ID NO:54)

<400> SEQUENCE: 53

-continued

```
Lys Gly Val Ser Leu Pro Tyr Arg Xaa
  1               5


<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (8)
<223> OTHER INFORMATION: Xaa = Arg linked with Xaa at position 9 of
      KGVSLPYRX (SEQ ID NO:53)

<400> SEQUENCE: 54

Lys Gly Val Ser Leu Pro Tyr Xaa
  1               5


<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSLSPR
      (SEQ ID NO:56)

<400> SEQUENCE: 55

Lys Gly Val Ser Leu Ser Pro Arg Xaa
  1               5


<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (8)
<223> OTHER INFORMATION: Xaa = Arg linked with Xaa at position 9 of
      KGVSLSPRX (SEQ ID NO:55)

<400> SEQUENCE: 56

Lys Gly Val Ser Leu Ser Pro Xaa
  1               5


<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Pro at position 8 of KGVSLSYP
      (SEQ ID NO:58)

<400> SEQUENCE: 57
```

-continued

```
Lys Gly Val Ser Leu Ser Tyr Pro Xaa
  1               5


<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (8)
<223> OTHER INFORMATION: Xaa = Pro linked with Xaa at position 9 of
      KGVSLSYPX (SEQ ID NO:57)

<400> SEQUENCE: 58

Lys Gly Val Ser Leu Ser Tyr Xaa
  1               5


<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 5 of each monomer sequence
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSP*SYR
      (SEQ ID NO:60)

<400> SEQUENCE: 59

Lys Gly Val Ser Xaa Ser Tyr Arg Xaa
  1               5


<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 5 of each monomer sequence
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (8)
<223> OTHER INFORMATION: Xaa = Arg linked with Xaa at position 9 of
      KGVSP*SYRX (SEQ ID NO:59)

<400> SEQUENCE: 60

Lys Gly Val Ser Xaa Ser Tyr Xaa
  1               5


<210> SEQ ID NO 61
```

-continued

```
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 6 of each monomer sequence
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSLP*YR
      (SEQ ID NO:62)

<400> SEQUENCE: 61

Lys Gly Val Ser Leu Xaa Tyr Arg Xaa
  1               5


<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 6 of each monomer sequence
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (8)
<223> OTHER INFORMATION: Xaa = Arg linked with Xaa at position 9 of
      KGVSLP*YRX (SEQ ID NO:61)

<400> SEQUENCE: 62

Lys Gly Val Ser Leu Xaa Tyr Xaa
  1               5


<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 7 of each monomer sequence
<220> FEATURE:
<221> NAME/KEY: MOD_RES
<222> LOCATION: (7)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker to the Arg at position 8 of KGVSLSP*R
      (SEQ ID NO:64)

<400> SEQUENCE: 63

Lys Gly Val Ser Leu Ser Xaa Arg Xaa
  1               5
```

-continued

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 7 of each monomer sequence
<220> FEATURE:
<221> NAME/KEY: MOD_RES
<222> LOCATION: (6)
<223> OTHER INFORMATION: Xaa = P* = proline-amino acid chimera
(3-aryl-proline,3-hydroxyaryl-proline or 3-alkyl-proline)
<220> FEATURE:
<221> NAME/KEY: MOD_RES
<222> LOCATION: (8)
<223> OTHER INFORMATION: Xaa = Arg linked with Xaa at position 9 of
KGVSLSP*RX (SEQ ID NO:63)

<400> SEQUENCE: 64

Lys Gly Val Ser Leu Ser Xaa Xaa
1 5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 8 of each monomer sequence
<220> FEATURE:
<221> NAME/KEY: MOD_RES
<222> LOCATION: (8)
<223> OTHER INFORMATION: Xaa = P* = proline-amino acid chimera
(3-aryl-proline,3-hydroxyaryl-proline or 3-alkyl-proline)
<220> FEATURE:
<221> NAME/KEY: MOD_RES
<222> LOCATION: (9)
<223> OTHER INFORMATION: Xaa = an amino acid like Lys, ornithine or any
other natural or unnatural amino acid serving as a
linker with the proline-amino acid
chimera (P*) at position 8 of KGVSLSYP* (SEQ ID NO:66)

<400> SEQUENCE: 65

Lys Gly Val Ser Leu Ser Tyr Xaa Xaa
1 5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 8 of each monomer sequence
<220> FEATURE:
<221> NAME/KEY: MOD_RES
<222> LOCATION: (8)
<223> OTHER INFORMATION: Xaa = P* = proline-amino acid chimera
(3-aryl-proline,3-hydroxyaryl-proline or 3-alkyl-proline) linked
with Xaa at position 9 of KGVSLSYP*X (SEQ ID NO:65)

<400> SEQUENCE: 66

Lys Gly Val Ser Leu Ser Tyr Xaa
1 5

<210> SEQ ID NO 67

-continued

<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with Bicyclic Turned Dipeptide (Btd) substituted
at residues 5 and 6 of each monomer sequence
<220> FEATURE:
<221> NAME/KEY: MOD_RES
<222> LOCATION: (5)..(6)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue
<220> FEATURE:
<221> NAME/KEY: MOD_RES
<222> LOCATION: (9)
<223> OTHER INFORMATION: Xaa = an amino acid like Lys, ornithine or any
other natural or unnatural amino acid serving as a
linker with the Arg at position 8 of KGVSBtdYR
(SEQ ID NO:68)

<400> SEQUENCE: 67

Lys Gly Val Ser Xaa Xaa Tyr Arg Xaa
1 5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with Bicyclic Turned Dipeptide (Btd) substituted
at residues 5 and 6 of each monomer sequence
<220> FEATURE:
<221> NAME/KEY: MOD_RES
<222> LOCATION: (5)..(6)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue
<220> FEATURE:
<221> NAME/KEY: MOD_RES
<222> LOCATION: (8)
<223> OTHER INFORMATION: Xaa = Arg linked with Xaa at position 9 of
KGVSBtdYRX (SEQ ID NO:67)

<400> SEQUENCE: 68

Lys Gly Val Ser Xaa Xaa Tyr Xaa
1 5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with Bicyclic Turned Dipeptide (Btd) substituted
at residues 6 and 7 of each monomer sequence
<220> FEATURE:
<221> NAME/KEY: MOD_RES
<222> LOCATION: (6)..(7)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue
<220> FEATURE:
<221> NAME/KEY: MOD_RES
<222> LOCATION: (9)

-continued

```
<223> OTHER INFORMATION: Xaa = an amino acid like Lys, ornithine or any
      other natural or unnatural amino acid serving as a
      linker with the Arg at position 8 of KGVSLBtdR
      (SEQ ID NO:70)

<400> SEQUENCE: 69

Lys Gly Val Ser Leu Xaa Xaa Arg Xaa
  1               5


<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 6 and 7 of each monomer sequence
<220> FEATURE:
<221> NAME/KEY: MOD_RES
<222> LOCATION: (6)..(7)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (8)
<223> OTHER INFORMATION: Xaa = Arg linked with Xaa at position 9 of
      KGVSLBtdRX (SEQ ID NO:69)

<400> SEQUENCE: 70

Lys Gly Val Ser Leu Xaa Xaa Xaa
  1               5


<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 7 and 8 of each monomer sequence
<220> FEATURE:
<221> NAME/KEY: MOD_RES
<222> LOCATION: (7)..(8)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (9)
<223> OTHER INFORMATION: Xaa = an amino acid like Lys, ornithine or any
      other natural or unnatural amino acid serving as a
      linker with the Bicyclic Turned Dipeptide (Btd) at
      position 8 of KGVSLSBtd (SEQ ID NO:72)

<400> SEQUENCE: 71

Lys Gly Val Ser Leu Ser Xaa Xaa Xaa
  1               5


<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
```

-continued

```
      at residues 7 and 8 of each monomer sequence
<220> FEATURE:
<221> NAME/KEY: MOD_RES
<222> LOCATION: (7)..(8)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
      linked to Xaa at position 9 of KGVSLSBtdX (SEQ ID NO:71)

<400> SEQUENCE: 72

Lys Gly Val Ser Leu Ser Xaa Xaa
  1               5


<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence:N-terminal
      sequence motif

<400> SEQUENCE: 73

Arg Phe Phe Glu Ser His
  1               5


<210> SEQ ID NO 74
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue having
      SDF-1[P2G] N-terminal residues 1-14 linked to
      C-terminal residues 55-67 by four Gly linker

<400> SEQUENCE: 74

Lys Gly Val Ser Leu Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30


<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue having
      SDF-1[P2G] N-terminal residues 1-17 linked to
      C-terminal residues 55-67 by four Gly linker

<400> SEQUENCE: 75

Lys Gly Val Ser Leu Ser Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn


<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue SDF-1[P2G]
      N-terminal residues 1-14 linked to C-terminal residues
```

-continued

```
      55-67 by -(CH-2)-n- linker
<220> FEATURE:
<221> NAME/KEY: MOD_RES
<222> LOCATION: (14)
<223> OTHER INFORMATION: Xaa = Phe linked via -(CH-2)-n-, where n = 1
      to 20,to Leu at position 1 of LKWIQEYLEKALN (SEQ ID NO:77)

<400> SEQUENCE: 76

Lys Gly Val Ser Leu Ser Tyr Arg Cys Pro Cys Arg Phe Xaa
  1               5                  10


<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue
      C-terminal residues 55-67 linked by -(CH-2)-n-
<220> FEATURE:
<221> NAME/KEY: MOD_RES
<222> LOCATION: (1)
<223> OTHER INFORMATION: Xaa = Leu linked via -(CH-2)-n-, where n = 1
      to 20, to the C-terminal amino acid of any one of SEQ ID NOS:76,
      78, 87-94, 103-110, and 117-122

<400> SEQUENCE: 77

Xaa Lys Trp Ile Gln Glu Tyr Leu Glu Lys Ala Leu Asn
  1               5                  10


<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue having
      SDF-1[P2G] N-terminal residues 1-17 linked to
      C-terminal residues 55-67 by -(CH-2)-n- linker
<220> FEATURE:
<221> NAME/KEY: MOD_RES
<222> LOCATION: (17)
<223> OTHER INFORMATION: Xaa = His linked via -(CH-2)-n-, where n = 1
      to 20, to Leu at position 1 of LKWIQEYLEKALN (SEQ ID NO:77)

<400> SEQUENCE: 78

Lys Gly Val Ser Leu Ser Tyr Arg Cys Pro Cys Arg Phe Phe Glu Ser
  1               5                  10                  15

Xaa


<210> SEQ ID NO 79
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer

<400> SEQUENCE: 79

Lys Gly Val Ser Pro Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30


<210> SEQ ID NO 80
<211> LENGTH: 31
<212> TYPE: PRT
<213> ORGANISM: Artificial Sequence
<220> FEATURE:
```

-continued

<223> OTHER INFORMATION: Description of Artificial Sequence:synthetic
SDF-1 CXCR4 receptor antagonist analogue dimer

<400> SEQUENCE: 80

```
Lys Gly Val Ser Leu Pro Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 81
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer

<400> SEQUENCE: 81

```
Lys Gly Val Ser Leu Ser Pro Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer

<400> SEQUENCE: 82

```
Lys Gly Val Ser Leu Ser Tyr Pro Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 83
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer

<400> SEQUENCE: 83

```
Lys Gly Val Ser Pro Ser Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn
```

<210> SEQ ID NO 84
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer

<400> SEQUENCE: 84

```
Lys Gly Val Ser Leu Pro Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
```

-continued

```
             20                  25                  30

Leu Asn


<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer

<400> SEQUENCE: 85

Lys Gly Val Ser Leu Ser Pro Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn


<210> SEQ ID NO 86
<211> LENGTH: 34
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer

<400> SEQUENCE: 86

Lys Gly Val Ser Leu Ser Tyr Pro Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn


<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 87

Lys Gly Val Ser Pro Ser Tyr Arg Cys Pro Cys Arg Phe Xaa
  1               5                  10


<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 88

Lys Gly Val Ser Leu Pro Tyr Arg Cys Pro Cys Arg Phe Xaa
  1               5                  10
```

-continued

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer
<220> FEATURE:
<221> NAME/KEY: MOD_RES
<222> LOCATION: (14)
<223> OTHER INFORMATION: Xaa = Phe linked via -(CH-2)-n-, where n = 1 to 20, to Leu at position 1 of LKWIQEYLEKALN (SEQ ID NO:77)

<400> SEQUENCE: 89

Lys Gly Val Ser Leu Ser Pro Arg Cys Pro Cys Arg Phe Xaa
1 5 10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer
<220> FEATURE:
<221> NAME/KEY: MOD_RES
<222> LOCATION: (14)
<223> OTHER INFORMATION: Xaa = Phe linked via -(CH-2)-n-, where n = 1 to 20, to Leu at position 1 of LKWIQEYLEKALN (SEQ ID NO:77)

<400> SEQUENCE: 90

Lys Gly Val Ser Leu Ser Tyr Pro Cys Pro Cys Arg Phe Xaa
1 5 10

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 91

Lys Gly Val Ser Pro Ser Tyr Arg Cys Pro Cys Arg Phe Phe Glu Ser
1 5 10 15

Xaa

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 92

Lys Gly Val Ser Leu Pro Tyr Arg Cys Pro Cys Arg Phe Phe Glu Ser
1 5 10 15

-continued

Xaa

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer
<220> FEATURE:
<221> NAME/KEY: MOD_RES
<222> LOCATION: (17)
<223> OTHER INFORMATION: Xaa = His linked via -(CH-2)-n-, where n = 1
to 20, to Leu at position 1 of LKWIQEYLEKALN (SEQ ID NO:77)

<400> SEQUENCE: 93

Lys Gly Val Ser Leu Ser Pro Arg Cys Pro Cys Arg Phe Phe Glu Ser
1 5 10 15

Xaa

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence:synthetic
SDF-1 CXCR4 receptor antagonist analogue dimer
<220> FEATURE:
<221> NAME/KEY: MOD_RES
<222> LOCATION: (17)
<223> OTHER INFORMATION: Xaa = His linked via -(CH-2)-n-, where n = 1
to 20, to Leu at position 1 of LKWIQEYLEKALN (SEQ ID NO:77)

<400> SEQUENCE: 94

Lys Gly Val Ser Leu Ser Tyr Pro Cys Pro Cys Arg Phe Phe Glu Ser
1 5 10 15

Xaa

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 5
<220> FEATURE:
<221> NAME/KEY: MOD_RES
<222> LOCATION: (5)
<223> OTHER INFORMATION: Xaa = P* = proline-amino acid chimera
(3-aryl-proline,3-hydroxyaryl-proline or 3-alkyl-proline)

<400> SEQUENCE: 95

Lys Gly Val Ser Xaa Ser Tyr Arg Cys Pro Cys Arg Phe Phe Gly Gly
1 5 10 15

Gly Gly Leu Lys Trp Ile Gln Glu Tyr Leu Glu Lys Ala Leu Asn
20 25 30

<210> SEQ ID NO 96
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 6
<220> FEATURE:

-continued

<221> NAME/KEY: MOD_RES
<222> LOCATION: (6)
<223> OTHER INFORMATION: Xaa = P* = proline-amino acid chimera
(3-aryl-proline,3-hydroxyaryl-proline or 3-alkyl-proline)

<400> SEQUENCE: 96

```
Lys Gly Val Ser Leu Xaa Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 97
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 7
<220> FEATURE:
<221> NAME/KEY: MOD_RES
<222> LOCATION: (7)
<223> OTHER INFORMATION: Xaa = P* = proline-amino acid chimera
(3-aryl-proline,3-hydroxyaryl-proline or 3-alkyl-proline)

<400> SEQUENCE: 97

```
Lys Gly Val Ser Leu Ser Xaa Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 98
<211> LENGTH: 31
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 8
<220> FEATURE:
<221> NAME/KEY: MOD_RES
<222> LOCATION: (8)
<223> OTHER INFORMATION: Xaa = P* = proline-amino acid chimera
(3-aryl-proline,3-hydroxyaryl-proline or 3-alkyl-proline)

<400> SEQUENCE: 98

```
Lys Gly Val Ser Leu Ser Tyr Xaa Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 5
<220> FEATURE:
<221> NAME/KEY: MOD_RES
<222> LOCATION: (5)
<223> OTHER INFORMATION: Xaa = P* = proline-amino acid chimera
(3-aryl-proline,3-hydroxyaryl-proline or 3-alkyl-proline)

<400> SEQUENCE: 99

-continued

Lys Gly Val Ser Xaa Ser Tyr Arg Cys Pro Cys Arg Phe Phe Glu Ser
1 5 10 15

His Gly Gly Gly Gly Leu Lys Trp Ile Gln Glu Tyr Leu Glu Lys Ala
20 25 30

Leu Asn

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 6
<220> FEATURE:
<221> NAME/KEY: MOD_RES
<222> LOCATION: (6)
<223> OTHER INFORMATION: Xaa = P* = proline-amino acid chimera
(3-aryl-proline,3-hydroxyaryl-proline or 3-alkyl-proline)

<400> SEQUENCE: 100

Lys Gly Val Ser Leu Xaa Tyr Arg Cys Pro Cys Arg Phe Phe Glu Ser
1 5 10 15

His Gly Gly Gly Gly Leu Lys Trp Ile Gln Glu Tyr Leu Glu Lys Ala
20 25 30

Leu Asn

<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 7
<220> FEATURE:
<221> NAME/KEY: MOD_RES
<222> LOCATION: (7)
<223> OTHER INFORMATION: Xaa = P* = proline-amino acid chimera
(3-aryl-proline,3-hydroxyaryl-proline or 3-alkyl-proline)

<400> SEQUENCE: 101

Lys Gly Val Ser Leu Ser Xaa Arg Cys Pro Cys Arg Phe Phe Glu Ser
1 5 10 15

His Gly Gly Gly Gly Leu Lys Trp Ile Gln Glu Tyr Leu Glu Lys Ala
20 25 30

Leu Asn

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with proline-amino acid chimera (P*) substituted
at residue 8
<220> FEATURE:
<221> NAME/KEY: MOD_RES
<222> LOCATION: (8)
<223> OTHER INFORMATION: Xaa = P* = proline-amino acid chimera
(3-aryl-proline,3-hydroxyaryl-proline or 3-alkyl-proline)

<400> SEQUENCE: 102

Lys Gly Val Ser Leu Ser Tyr Xaa Cys Pro Cys Arg Phe Phe Glu Ser

-continued

```
 1               5                   10                  15

His Gly Gly Gly Gly Leu Lys Trp Ile Gln Glu Tyr Leu Glu Lys Ala
             20                  25                  30

Leu Asn


<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 5
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 103

Lys Gly Val Ser Xaa Ser Tyr Arg Cys Pro Cys Arg Phe Xaa
 1               5                   10


<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 6
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 104

Lys Gly Val Ser Leu Xaa Tyr Arg Cys Pro Cys Arg Phe Xaa
 1               5                   10


<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 7
<220> FEATURE:
<221> NAME/KEY: MOD_RES
<222> LOCATION: (7)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)
```

-continued

```
<400> SEQUENCE: 105

Lys Gly Val Ser Leu Ser Xaa Arg Cys Pro Cys Arg Phe Xaa
  1               5                   10


<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 8
<220> FEATURE:
<221> NAME/KEY: MOD_RES
<222> LOCATION: (8)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 106

Lys Gly Val Ser Leu Ser Tyr Xaa Cys Pro Cys Arg Phe Xaa
  1               5                   10


<210> SEQ ID NO 107
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 5
<220> FEATURE:
<221> NAME/KEY: MOD_RES
<222> LOCATION: (5)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (17)
<223> OTHER INFORMATION: Xaa = His linked via -(CH-2)-n-, where n = 1
      to 20, to Leu at position 1 of LKWIQEYLEKALN (SEQ ID NO:77)

<400> SEQUENCE: 107

Lys Gly Val Ser Xaa Ser Tyr Arg Cys Pro Cys Arg Phe Phe Glu Ser
  1               5                   10                  15

Xaa


<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with proline-amino acid chimera (P*) substituted
      at residue 6
<220> FEATURE:
<221> NAME/KEY: MOD_RES
<222> LOCATION: (6)
<223> OTHER INFORMATION: Xaa = P* = proline-amino acid chimera
      (3-aryl-proline,3-hydroxyaryl-proline or 3-alkyl-proline)
<220> FEATURE:
<221> NAME/KEY: MOD_RES
<222> LOCATION: (17)
<223> OTHER INFORMATION: Xaa = His linked via -(CH-2)-n-, where n = 1
```

-continued to 20, to Leu at position 1 of LKWIQEYLEKALN (SEQ ID NO:77)

<400> SEQUENCE: 108

Lys Gly Val Ser Leu Xaa Tyr Arg Cys Pro Cys Arg Phe Phe Glu Ser
1 5 10 15

Xaa

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with proline-amino acid chimera (P*) substituted at residue 7
<220> FEATURE:
<221> NAME/KEY: MOD_RES
<222> LOCATION: (7)
<223> OTHER INFORMATION: Xaa = P* = proline-amino acid chimera (3-aryl-proline,3-hydroxyaryl-proline or 3-alkyl-proline)
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 109

Lys Gly Val Ser Leu Ser Xaa Arg Cys Pro Cys Arg Phe Phe Glu Ser
1 5 10 15

Xaa

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with proline-amino acid chimera (P*) substituted at residue 8
<220> FEATURE:
<221> NAME/KEY: MOD_RES
<222> LOCATION: (8)
<223> OTHER INFORMATION: Xaa = P* = proline-amino acid chimera (3-aryl-proline,3-hydroxyaryl-proline or 3-alkyl-proline)
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 110

Lys Gly Val Ser Leu Ser Tyr Xaa Cys Pro Cys Arg Phe Phe Glu Ser
1 5 10 15

Xaa

<210> SEQ ID NO 111
<211> LENGTH: 31
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide -continued (3-carboxy-5-oxo-6-amino-1,2,7,8,9-pentahydro-indolizine, [1-alkyl/aryl/hydroxyaryl]-3-carboxy-5- oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 111

```
Lys Gly Val Ser Xaa Xaa Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 112
<211> LENGTH: 31
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5- oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 112

```
Lys Gly Val Ser Leu Xaa Xaa Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 113
<211> LENGTH: 31
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5- oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue

<400> SEQUENCE: 113

```
Lys Gly Val Ser Leu Ser Xaa Xaa Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30
```

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 5 and 6
<220> FEATURE:
<221> NAME/KEY: MOD_RES -continued
<222> LOCATION: (5)..(6)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 114

```
Lys Gly Val Ser Xaa Xaa Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn
```

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with Bicyclic Turned Dipeptide (Btd) substituted
at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 115

```
Lys Gly Val Ser Leu Xaa Xaa Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn
```

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence:synthetic
SDF-1[P2G] CXCR4 receptor antagonist analogue dimer
with Bicyclic Turned Dipeptide (Btd) substituted
at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide
(3-carboxy-5-oxo-6-amino-1,2,7,8,9-pentahydro-indolizine,
[1-alkyl/aryl/hydroxyaryl]-3-carboxy-5- oxo-6-amino-2,7,8,9-
tetrahydro-indolizine or 3-carboxy-5-oxo-6-amino-[8-alkyl/aryl/
hydroxyaryl]-1,2,7,9-tetrahydro-indolizine) single residue

<400> SEQUENCE: 116

```
Lys Gly Val Ser Leu Ser Xaa Xaa Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn
```

<210> SEQ ID NO 117
<211> LENGTH: 14
<212> TYPE: PRT

-continued

```
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 117

Lys Gly Val Ser Xaa Xaa Tyr Arg Cys Pro Cys Arg Phe Xaa
  1               5                  10


<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 118

Lys Gly Val Ser Leu Xaa Xaa Arg Cys Pro Cys Arg Phe Xaa
  1               5                  10


<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist analogue dimer
      with Bicyclic Turned Dipeptide (Btd) substituted
      at residues 7 and 8
<220> FEATURE:
<221> NAME/KEY: MOD_RES
<222> LOCATION: (7)..(8)
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Leu at position 1 of LKWIQEYLEKALN (SEQ ID NO:77)

<400> SEQUENCE: 119
```

-continued

Lys Gly Val Ser Leu Ser Xaa Xaa Cys Pro Cys Arg Phe Xaa
1 5 10

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 5 and 6
<220> FEATURE:
<221> NAME/KEY: MOD_RES
<222> LOCATION: (5)..(6)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5- oxo-6-amino-2,7,8,9-tetrahydro-indolizine or 3-carboxy-5-oxo-6-amino-[8-alkyl/aryl/hydroxyaryl]-1,2,7,9-tetrahydro-indolizine) single residue
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 120

Lys Gly Val Ser Xaa Xaa Tyr Arg Cys Pro Cys Arg Phe Phe Glu Ser
1 5 10 15

Xaa

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 6 and 7
<220> FEATURE:
<221> NAME/KEY: MOD_RES
<222> LOCATION: (6)..(7)
<223> OTHER INFORMATION: Xaa = Btd = Bicyclic Turned Dipeptide (3-carboxy-5-oxo-6-amino-1,2,7,8,9-pentahydro-indolizine, [1-alkyl/aryl/hydroxyaryl]-3-carboxy-5- oxo-6-amino-2,7,8,9-tetrahydro-indolizine or 3-carboxy-5-oxo-6-amino -[8-alkyl/aryl/hydroxyaryl]-1,2,7,9-tetrahydro-indolizine)
<220> FEATURE:
<221> NAME/KEY: MOD_RES
<222> LOCATION: (17)
<223> OTHER INFORMATION: Xaa = His linked via -(CH-2)-n-, where n = 1 to 20, to Leu at position 1 of LKWIQEYLEKALN (SEQ ID NO:77)

<400> SEQUENCE: 121

Lys Gly Val Ser Leu Xaa Xaa Arg Cys Pro Cys Arg Phe Phe Glu Ser
1 5 10 15

Xaa

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence:synthetic SDF-1[P2G] CXCR4 receptor antagonist analogue dimer with Bicyclic Turned Dipeptide (Btd) substituted at residues 7 and 8
<220> FEATURE:
<221> NAME/KEY: MOD_RES
<222> LOCATION: (7)..(8)

-continued

```
<223> OTHER INFORMATION: Xaa = Btd = Bicyclic Turned Dipeptide
      (3-carboxy-5-oxo-6-amino-1,2,7,8,9-pentahydro-indolizine,
      [1-alkyl/aryl/hydroxyaryl]-3-carboxy-5- oxo-6-amino-2,7,8,9-
      tetrahydro-indolizine or 3-carboxy-5-oxo-6-amino-[8-alkyl/aryl/
      hydroxyaryl]-1,2,7,9-tetrahydro-indolizine) single residue
<220> FEATURE:
<221> NAME/KEY: MOD_RES
<222> LOCATION: (17)
<223> OTHER INFORMATION: Xaa = His linked via -(CH-2)-n-, where n = 1
      to 20, to Leu at position 1 of LKWIQEYLEKALN (SEQ ID NO:77)

<400> SEQUENCE: 122

Lys Gly Val Ser Leu Ser Xaa Xaa Cys Pro Cys Arg Phe Phe Glu Ser
  1               5                  10                  15

Xaa


<210> SEQ ID NO 123
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue
<220> FEATURE:
<221> NAME/KEY: misc_feature
<222> LOCATION: (20)..(24)
<223> OTHER INFORMATION: K20/E24 cyclization by 2-lactamization

<400> SEQUENCE: 123

Lys Gly Val Ser Leu Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Asn
             20                  25                  30


<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue
<220> FEATURE:
<221> NAME/KEY: misc_feature
<222> LOCATION: (23)..(27)
<223> OTHER INFORMATION: K23/E27 cyclization by 2-lactamization

<400> SEQUENCE: 124

Lys Gly Val Ser Leu Ser Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
             20                  25                  30

Leu Asn


<210> SEQ ID NO 125
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue
<220> FEATURE:
<221> NAME/KEY: misc_feature
<222> LOCATION: (24)..(28)
<223> OTHER INFORMATION: E24/K28 cyclization by 2-lactamization

<400> SEQUENCE: 125

Lys Gly Val Ser Leu Ser Tyr Arg Cys Pro Cys Arg Phe Phe Gly Gly
  1               5                  10                  15
```

-continued

```
Gly Gly Leu Lys Trp Ile Gln Glu Tyr Leu Glu Lys Ala Leu Asn
            20                  25                  30


<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue
<220> FEATURE:
<221> NAME/KEY: misc_feature
<222> LOCATION: (27)..(31)
<223> OTHER INFORMATION: E27/K31 cyclization by 2-lactamization

<400> SEQUENCE: 126

Lys Gly Val Ser Leu Ser Tyr Arg Cys Pro Cys Arg Phe Phe Glu Ser
  1               5                  10                  15

His Gly Gly Gly Gly Leu Lys Trp Ile Gln Glu Tyr Leu Glu Lys Ala
            20                  25                  30

Leu Asn


<210> SEQ ID NO 127
<211> LENGTH: 33
<212> TYPE: PRT
<213> ORGANISM: Artificial Sequence
<220> FEATURE:
<223> OTHER INFORMATION: Description of Artificial Sequence:synthetic
      CXCR4 receptor antagonist SDF-1[P2G](1-14)/MIP-1alpha(36-50)
      hybrid analog

<400> SEQUENCE: 127

Lys Gly Val Ser Leu Ser Tyr Arg Cys Pro Cys Arg Phe Phe Gly Gly
  1               5                  10                  15

Gly Gly Ser Lys Pro Gly Val Ile Phe Leu Thr Lys Arg Ser Arg Gln
            20                  25                  30

Val


<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence:synthetic
      CXCR4 receptor antagonist SDF-1[P2G](1-14)/MIP-1alpha(36-50)
      hybrid analog
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Ser at position 1 of SKPGVIFLTKRSRQV (SEQ ID NO:129)

<400> SEQUENCE: 128

Lys Gly Val Ser Leu Ser Tyr Arg Cys Pro Cys Arg Phe Xaa
  1               5                  10


<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist hybrid analog
      MIP-1alpha GAG-binding residues 36-50 linked by
      -(CH-2)-n-
<220> FEATURE:
<221> NAME/KEY: MOD_RES
```

-continued

```
<222> LOCATION: (1)
<223> OTHER INFORMATION: Xaa = Ser linked via -(CH-2)-n-, where n = 1
      to 20, to Phe at position 14 of KGVSLSYRCPCRFF (SEQ ID NO:128)

<400> SEQUENCE: 129

Xaa Lys Pro Gly Val Ile Phe Leu Thr Lys Arg Ser Arg Gln Val
  1               5                  10                  15


<210> SEQ ID NO 130
<211> LENGTH: 33
<212> TYPE: PRT
<213> ORGANISM: Artificial Sequence
<220> FEATURE:
<223> OTHER INFORMATION: Description of Artificial Sequence:synthetic
      CXCR4 receptor antagonist SDF-1[P2G](1-14)/MIP-1alpha(55-70)
      hybrid analog

<400> SEQUENCE: 130

Lys Gly Val Ser Leu Ser Tyr Arg Cys Pro Cys Arg Phe Phe Gly Gly
  1               5                  10                  15

Gly Gly Glu Glu Trp Val Gln Lys Tyr Val Asp Asp Leu Glu Leu Ser

             20                  25                  30
Ala


<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence:synthetic
      CXCR4 receptor antagonist SDF-1[P2G](1-14)/MIP-1alpha(55-70)
      hybrid analog
<220> FEATURE:
<221> NAME/KEY: MOD_RES
<222> LOCATION: (14)
<223> OTHER INFORMATION: Xaa = Phe linked via -(CH-2)-n-, where n = 1
      to 20, to Glu at position 1 of EEWVQKYVDDLELSA (SEQ ID NO:132)

<400> SEQUENCE: 131

Lys Gly Val Ser Leu Ser Tyr Arg Cys Pro Cys Arg Phe Xaa
  1               5                  10


<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence:synthetic
      SDF-1[P2G] CXCR4 receptor antagonist hybrid analog
      MIP-1alpha GAG-binding residues 55-70 linked by
      -(CH-2)-n-
<220> FEATURE:
<221> NAME/KEY: MOD_RES
<222> LOCATION: (1)
<223> OTHER INFORMATION: Xaa = Glu linked via -(CH-2)-n-, where n = 1
      to 20, to Phe at position 14 of KGVSLSYRCPCRFF (SEQ ID NO:131)

<400> SEQUENCE: 132

Xaa Glu Trp Val Gln Lys Tyr Val Asp Asp Leu Glu Leu Ser Ala
  1               5                  10                  15


<210> SEQ ID NO 133
<211> LENGTH: 67
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue CTCE0012
```

<400> SEQUENCE: 133

Lys Gly Val Ser Leu Ser Tyr Arg Cys Pro Cys Arg Phe Phe Glu Ser
1 5 10 15

His Val Ala Arg Ala Asn Val Lys His Leu Lys Ile Leu Asn Thr Pro
20 25 30

Ala Cys Ala Leu Gln Ile Val Ala Arg Leu Lys Asn Asn Asn Arg Gln
35 40 45

Val Cys Ile Asp Pro Lys Leu Lys Trp Ile Gln Glu Tyr Leu Glu Lys
50 55 60

Ala Leu Asn
65

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer CTCE9908
<220> FEATURE:
<221> NAME/KEY: MOD_RES
<222> LOCATION: (9)
<223> OTHER INFORMATION: Xaa = Lys-CONH-2 linked to the Arg at position 8 of KGVSLSYR (SEQ ID NO:135)

<400> SEQUENCE: 134

Lys Gly Val Ser Leu Ser Tyr Arg Xaa
1 5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer CTCE9908
<220> FEATURE:
<221> NAME/KEY: MOD_RES
<222> LOCATION: (8)
<223> OTHER INFORMATION: Xaa = Arg liked to Lys-CONH2 at position 9 of KGVSLSYRK-CONH-2 (SEQ ID NO:134)

<400> SEQUENCE: 135

Lys Gly Val Ser Leu Ser Tyr Xaa
1 5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence:synthetic SDF-1 CXCR4 receptor antagonist analogue dimer CTCE9907
<220> FEATURE:
<221> NAME/KEY: AMIDATION
<222> LOCATION: (9)
<223> OTHER INFORMATION: cysteinamide
<220> FEATURE:
<221> NAME/KEY: MOD_RES
<222> LOCATION: (9)
<223> OTHER INFORMATION: Xaa = cysteinamide disulphide linked to the cysteinamide at position 9 of KGVSLSYRC(CONH-2) (SEQ ID NO:136)
<220> FEATURE:
<221> NAME/KEY: DISULFID
<222> LOCATION: (9)
<223> OTHER INFORMATION: dimer of amino acids 1-9 in which the amino -continued

```
      acid chains are joined by a disulphide bond between
      each of the cysteinamides at position 9 in each
      sequence

<400> SEQUENCE: 136

Lys Gly Val Ser Leu Ser Tyr Arg Xaa
  1               5


<210> SEQ ID NO 137
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
      CTCE0018
<220> FEATURE:
<221> NAME/KEY: AMIDATION
<222> LOCATION: (31)
<223> OTHER INFORMATION: asparaginamide
<220> FEATURE:
<221> NAME/KEY: MOD_RES
<222> LOCATION: (31)
<223> OTHER INFORMATION: Xaa = asparaginamide

<400> SEQUENCE: 137

Lys Gly Val Ser Leu Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Xaa
             20                  25                  30


<210> SEQ ID NO 138
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
      CTCE0019
<220> FEATURE:
<221> NAME/KEY: misc_feature
<222> LOCATION: (20)..(24)
<223> OTHER INFORMATION: K20/E24 cyclization by 2-lactamization
<220> FEATURE:
<221> NAME/KEY: AMIDATION
<222> LOCATION: (31)
<223> OTHER INFORMATION: asparaginamide
<220> FEATURE:
<221> NAME/KEY: MOD_RES
<222> LOCATION: (31)
<223> OTHER INFORMATION: Xaa = asparaginamide

<400> SEQUENCE: 138

Lys Gly Val Ser Leu Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Xaa
             20                  25                  30


<210> SEQ ID NO 139
<211> LENGTH: 31
<212> TYPE: PRT
<213> ORGANISM: Artificial Sequence
<220> FEATURE:
<223> OTHER INFORMATION: Description of Artificial Sequence:synthetic
      SDF-1 CXCR4 receptor antagonist analogue dimer
      CTCE0020
<220> FEATURE:
<221> NAME/KEY: misc_feature
<222> LOCATION: (24)..(28)
<223> OTHER INFORMATION: E24/K28 cyclization by 2-lactamization
<220> FEATURE:
```

-continued

```
<221> NAME/KEY: AMIDATION
<222> LOCATION: (31)
<223> OTHER INFORMATION: asparaginamide
<220> FEATURE:
<221> NAME/KEY: MOD_RES
<222> LOCATION: (31)
<223> OTHER INFORMATION: Xaa = asparaginamide

<400> SEQUENCE: 139

Lys Gly Val Ser Leu Ser Tyr Arg Cys Pro Cys Arg Phe Phe Gly Gly
  1               5                  10                  15

Gly Gly Leu Lys Trp Ile Gln Glu Tyr Leu Glu Lys Ala Leu Xaa
             20                  25                  30


<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence:N-terminal
      residues which form a beta-turn

<400> SEQUENCE: 140

Leu Ser Tyr Arg
  1
```

What is claimed is:

1. A composition comprising a CXCR4 antagonist selected from the group consisting of:

1) a first SDF-1 analog having CXCR4 antagonist activity consisting of:

(i) an N-terminal region consisting of from 14 to about 17 amino acids that comprise a conserved KGVS (residues 1-4 in SEQ ID NO:1) motif in residue positions 1-4, and a conserved CPCRFF (residues 9-14 in SEQ ID NO:1) in residue positions 9-14;

(ii) a C-terminal region consisting of LKWIQEYLEKALN (residues 55-67 in SEQ ID NO:1); and (iii) a linker consisting of either 4 natural amino acids or an aminoalkanoic acid having up to 20 carbons, where the linker connects the N-terminal region to the C-terminal region to form the CXCR4 antagonist; and 2) a second SDF-1 analog having CXCR4 antagonist activity, said second SDF-1 analog consisting of the first SDF-1 analog having conservative amino acid substitutions, wherein the conservative amino acid substitutions occur in any of residues 9-14 of the N-terminal region or the C-terminal region; and wherein the first or second SDF-1 analog is optionally modified with an acyl group, acetyl group, an amide group, a detectable substance, a modifier capable of reducing the ability of the analog to act as a substrate for carboxypeptidases, or a modifier capable of reducing the ability of the analog to act as a substrate for aminopeptidases.

2. The composition of claim 1, wherein the N-terminal region of the SDF-1 analog consists of KGVSLSYRCPCRFF (residues 1-14 of SEQ ID NO:13).

3. The composition of claim 1, wherein the N-terminal region of the SDF-1 analog consists of KGVSLSYRCPCRFFESH (SEQ ID NO:13).

4. The composition of claim 1, wherein the linker is GGGG (residues 15-18 of SEQ ID NO:74).

5. The composition of claim 1, wherein the C-terminal region of the SDF-1 analog is cyclized at residue positions corresponding to $K^{56}$ and $E^{60}$ of SEQ ID NO:1.

6. The composition of claim 1, wherein the C-terminal region of the SDF-1 analog is cyclized at residue positions corresponding to $E^{60}$ and $K^{64}$ of SEQ ID NO:1.

7. A composition comprising a CXCR4 antagonist selected from the group consisting of SEQ ID NOs: 74, 75, 137, 138, and 139.

8. The composition of claim 1, wherein the SDF-1 analog is modified with an acyl group, acetyl group, an amide group, a detectable substance, a modifier capable of reducing the ability of the analog to act as a substrate for carboxypeptidases, or a modifier capable of reducing the ability of the analog to act as a substrate for aminopeptidases.

9. A pharmaceutical composition comprising the composition of claim 1 and a pharmaceutically acceptable carrier.

10. A composition comprising an SDF-1 analog having CXCR4 antagonist activity, said SDF-1 analog consisting of:

(i) an N-terminal region selected from the group consisting of:

a) residues 1-14 of SEQ ID NO:1, b) residues 1-15 of SEQ ID NO:1, c) residues 1-16 of SEQ ID NO:1, and d) residues 1-17 of SEQ ID NO:1;

(ii) a C-terminal region consisting of LKWIQEYLEKALN (residues 55-67 in SEQ ID NO:1); and (iii) a linker consisting of either 4 natural amino acids or an aminoalkanoic acid having up to 20 carbons, where the linker connects the N-terminal region to the C-terminal region to form the CXCR4 antagonist;

wherein the SDF-1 analog is optionally modified with an acyl group, acetyl group, an amide group, a detectable substance, a modifier capable of reducing the ability of the analog to act as a substrate for carboxypeptidases, or a modifier capable of reducing the ability of the analog to act as a substrate for aminopeptidases.

11. The composition of claim 10, wherein the C-terminal region of the SDF-1 analog is cyclized at residue positions corresponding to $K^{56}$ and $E^{60}$ of SEQ ID NO: 1.

12. The composition of claim 10, wherein the C-terminal region of the SDF-1 analog is cyclized at residue positions corresponding to $E^{60}$ and $K^{64}$ of SEQ ID NO: 1.

13. The composition of claim 10, wherein the SDF-1 analog is modified with an acyl group, acetyl group, an amide group, a detectable substance, a modifier capable of reducing the ability of the analog to act as a substrate for carboxypeptidases, or a modifier capable of reducing the ability of the analog to act as a substrate for aminopeptidases.

14. A pharmaceutical composition comprising the composition of claim 10 and a pharmaceutically acceptable carrier.

* * * * *